(12) United States Patent
Nakaminami et al.

(10) Patent No.: US 7,816,145 B2
(45) Date of Patent: Oct. 19, 2010

(54) METHOD, DEVICE AND APPARATUS FOR MEASURING THE CONCENTRATION OF CREATININE, AND METHOD, DEVICE AND APPARATUS FOR MEASURING THE AMOUNT OF SALT USING THE SAME

(75) Inventors: Takahiro Nakaminami, Ehime (JP); Kouji Kashiwada, Osaka (JP); Atsushi Fukunaga, Fukuoka (JP)

(73) Assignee: Panasonic Corporation, Osaka (JP)

( * ) Notice: Subject to any disclaimer, the term of this patent is extended or adjusted under 35 U.S.C. 154(b) by 0 days.

(21) Appl. No.: 12/717,493

(22) Filed: Mar. 4, 2010

(65) Prior Publication Data

US 2010/0159606 A1 Jun. 24, 2010

Related U.S. Application Data

(63) Continuation of application No. PCT/JP2009/002166, filed on May 15, 2009.

(30) Foreign Application Priority Data

May 16, 2008 (JP) ............................. 2008-129380
May 26, 2008 (JP) ............................. 2008-136225

(51) Int. Cl.
*G01N 33/00* (2006.01)
(52) U.S. Cl. .............................. 436/98; 436/96; 436/91; 356/72
(58) Field of Classification Search ................... 436/98, 436/96, 91; 356/72
See application file for complete search history.

(56) References Cited

U.S. PATENT DOCUMENTS

| 3,705,013 A | | 12/1972 | Dewhurst et al. | |
|---|---|---|---|---|
| 3,964,974 A | * | 6/1976 | Banauch et al. | ................. 435/4 |
| 4,215,197 A | | 7/1980 | Tarbutton | |
| 4,812,399 A | | 3/1989 | Mauck et al. | |

(Continued)

FOREIGN PATENT DOCUMENTS

JP 54-151095 11/1979

(Continued)

OTHER PUBLICATIONS

MacNeil et al., Analysis of creatine, creatinine, creatine-d3 and creatinine-d3 in urine, plasma, and red blood cells by HPLC and GC-MS to follow the fate of ingested creatine-d3, 2005, Journal of Chromatogrpahy B, 827, 210-215.*

(Continued)

*Primary Examiner*—Yelena G Gakh
*Assistant Examiner*—David Weisz
(74) *Attorney, Agent, or Firm*—McDermott Will & Emery LLP

(57) ABSTRACT

A method for measuring a concentration of creatinine includes the steps of: (A) mixing a sample containing creatinine with a creatinine quantitative reagent containing a metal complex of at least one of hexacyanoferrate and hexacyanoruthenate in the absence of picric acid and any enzyme responsive to creatinine, to cause the creatinine to reduce the metal complex; (B) electrochemically or optically measuring the amount of the metal complex reduced in the step (A); and (C) determining the concentration of the creatinine contained in the sample from the amount of the reduced metal complex measured in the step (B).

7 Claims, 13 Drawing Sheets

U.S. PATENT DOCUMENTS

| | | | |
|---|---|---|---|
| 5,047,329 A | 9/1991 | Suzuki | |
| 5,141,868 A | 8/1992 | Shanks et al. | |
| 5,466,575 A | 11/1995 | Cozzette et al. | |
| 6,861,232 B2 * | 3/2005 | Schaffar | 435/7.91 |

FOREIGN PATENT DOCUMENTS

| | | |
|---|---|---|
| JP | 55-023998 | 2/1980 |
| JP | 62-257400 | 11/1987 |
| JP | 63-033661 | 2/1988 |
| JP | 63-182000 | 7/1988 |
| JP | 07-248310 | 9/1995 |
| JP | 09-061430 | 3/1997 |
| JP | 09-127126 | 5/1997 |
| JP | 2001-512692 | 8/2001 |
| JP | 2003-326172 | 11/2003 |
| JP | 2003-533679 | 11/2003 |
| JP | 2004-138407 | 5/2004 |
| JP | 2005-118014 | 5/2005 |
| JP | 2006-349412 | 12/2006 |
| JP | 2008-070346 | 3/2008 |
| WO | WO 99/07881 | 2/1999 |
| WO | WO 01/87300 A1 | 11/2001 |

OTHER PUBLICATIONS

Sullivan, M.X., et al., "A Highly Specific Test for Creatinine", The Journal of Biological Chemistry, Aug. 1958, pp. 530-534, vol. 233 No. 2.

Narayanan, S., et al., "Creatinine: A Review", Clinical Chemistry, 1980, pp. 1119-1126, vol. 26 No. 8.

Cooper, J., et al., "An Evaluation of Four Methods of Measuring Urinary Creatinine", Clinical Chemistry, 1961, pp. 665-673, vol. 7 No. 6.

Japanese Office Action issued in Japanese Patent Application No. 2009-541527, mailed Dec. 17, 2009.

Kayser, F., et al., "Quantification of creatinine by potassium ferricyanide", Annales De Biologie Clinique, pp. 219-222, with English translation, Mar. 1956.

* cited by examiner

F I G. 2
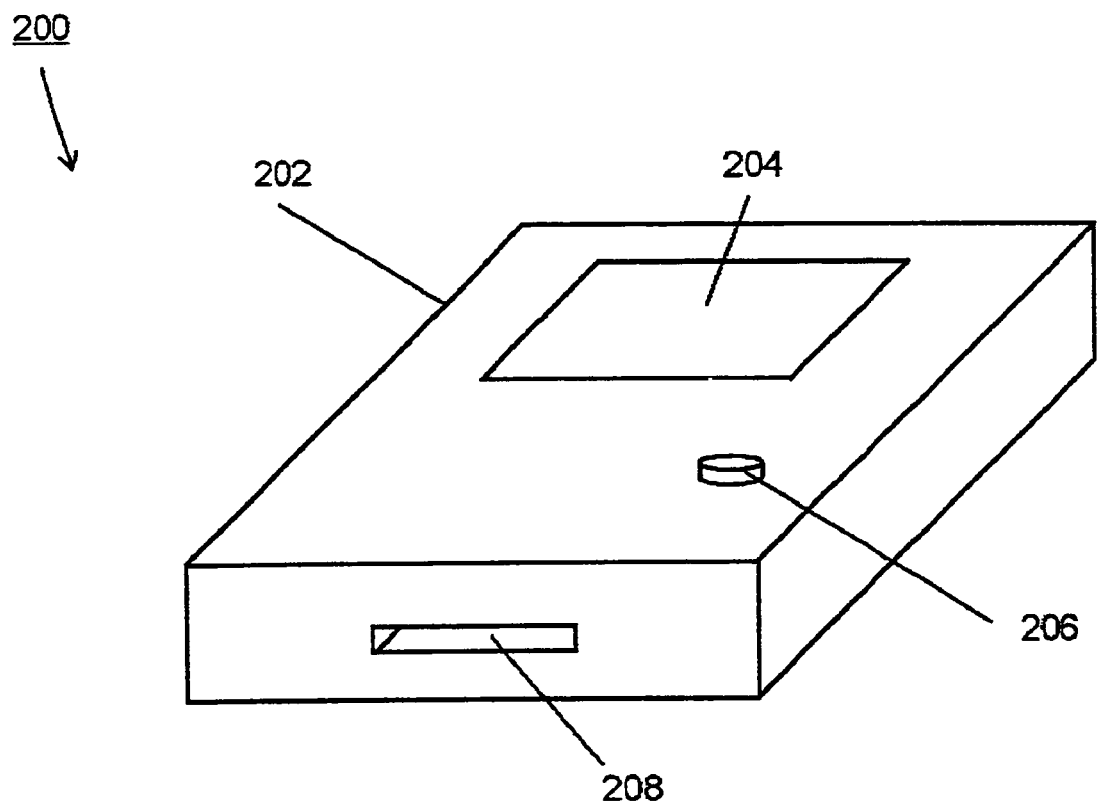

[FIG. 11]
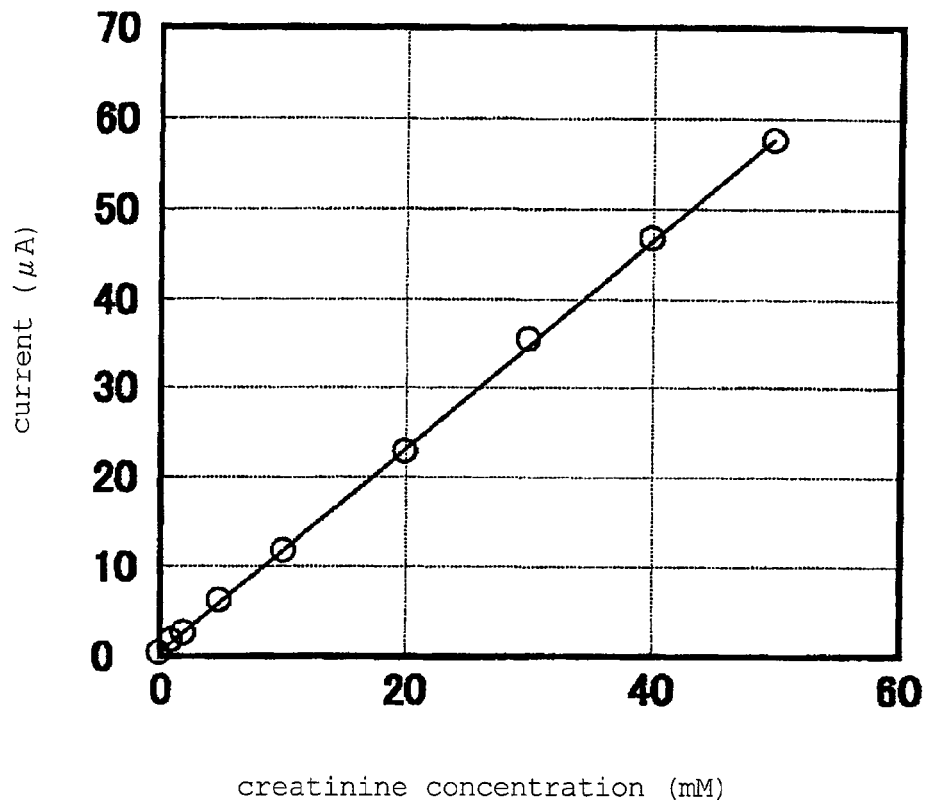
[FIG. 12]
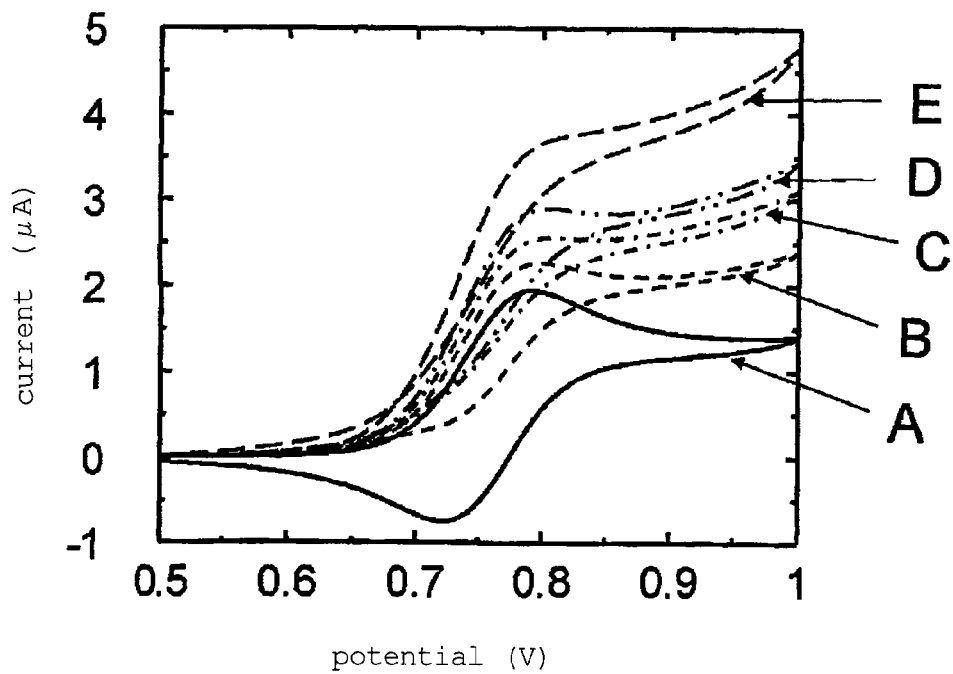

[FIG. 13]
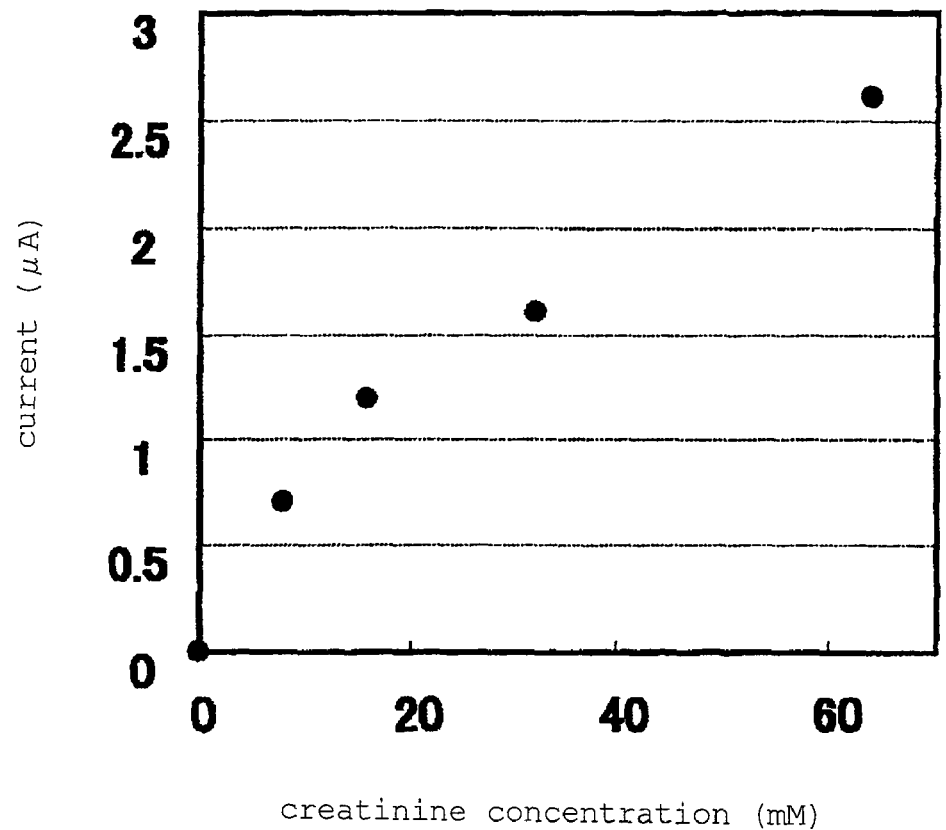
[FIG. 14]
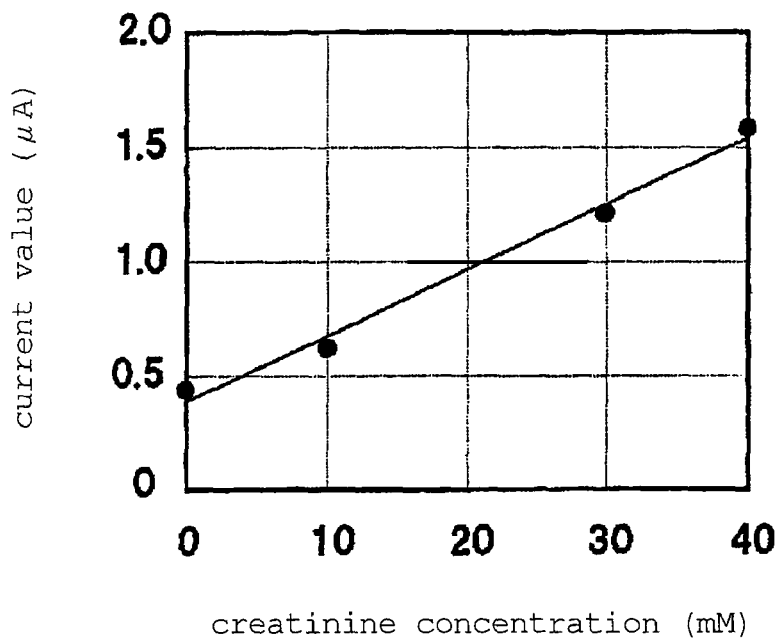

[FIG. 15]
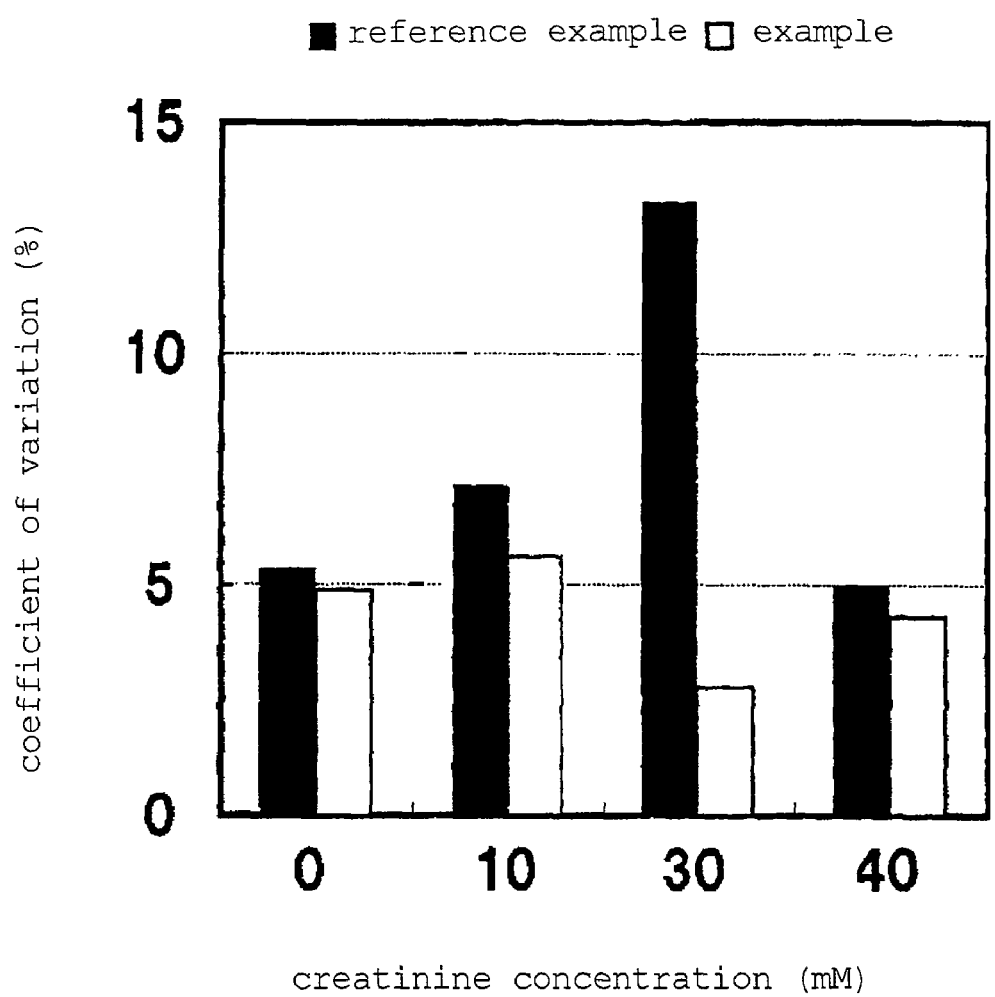

METHOD, DEVICE AND APPARATUS FOR MEASURING THE CONCENTRATION OF CREATININE, AND METHOD, DEVICE AND APPARATUS FOR MEASURING THE AMOUNT OF SALT USING THE SAME

This application is a continuation of International Application No. PCT/JP2009/002166, whose international filing date is May 15, 2009, which in turn claims the benefit of Japanese Patent Application No. 2008-129380, filed on May 16, 2008 and Japanese Patent Application No. 2008-136225, filed on May 26, 2008, the disclosures of which Applications are incorporated by reference herein. The benefit of the filing and priority dates of the International and Japanese Applications is respectfully requested.

TECHNICAL FIELD

The invention relates to a measurement method, device, and apparatus for quantifying creatinine or salt contained in a sample.

BACKGROUND ART

The measurement of the concentration of creatinine contained in a sample is important in the fields of clinical chemistry and analytical chemistry. Since creatinine is a product of the endogenous metabolism of muscle, it is known that the amount of creatinine in urine reflects total muscle mass. Hence, it is believed that the amount of creatinine excretion in the urine of each individual in a day is usually constant and does not vary from day to day. As such, the amount of urinary creatinine may be used as a measure of the thickness of excreted urine. Also, the amount of creatinine in urine and blood increases/decreases due to uremia or decreased renal function. Thus, the measurement of the amount of creatinine in urine or blood permits determination of the presence or absence of uremia or decreased renal function.

A known method for measuring creatinine concentration is a method based on Jaffe reaction using an alkaline picrate solution. According to this method, the orange-red product formed by the reaction between picric acid and creatinine is spectroscopically measured (see, for example, PTL 1).

Another known method for measuring creatinine concentration is a method using an enzyme that reacts specifically with creatinine. An example of such an enzymatic method is a method of decomposing creatinine using creatinine deiminase (see, for example, PTL 2). According to this method, the amount of ammonia produced by the decomposition of creatinine is measured based on the change in pH, potential, or the like to determine creatinine concentration.

Another enzymatic method is a method of measuring creatinine concentration by carrying out the following reactions of formulas (1) to (3).

Creatinine+Water→Creatine  (1)

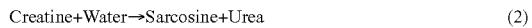

Creatine+Water→Sarcosine+Urea  (2)

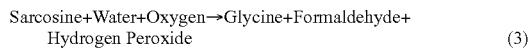

Sarcosine+Water+Oxygen→Glycine+Formaldehyde+
Hydrogen Peroxide  (3)

The enzymes used to catalyze the reactions of formulas (1) to (3) are creatinine amidohydrolase (creatininase), creatine amidinohydrolase (creatinase), and sarcosine oxidase or sarcosine dehydrogenase, respectively. Creatinine is quantified, for example, by a method of using a leuco pigment and the Trinder reagent together with a peroxidase to cause the hydrogen peroxide produced in formula (3) to give a color for spectroscopic quantification (see, for example, PTL 3). Also, another creatinine quantification method is a method of electrochemically oxidizing the hydrogen peroxide produced in formula (3) at an electrode to cause a current to flow and quantifying creatinine from the current (see, for example, PTLs 4 and 5).

Further, still another enzymatic method is a method of quantifying creatinine by carrying out the reactions of formulas (1) and (2) and additionally carrying out the reaction between sarcosine and an electron mediator (mediator) instead of the reaction of formula (3) (see, for example, PTLs 6 and 7).

PTL 6 discloses a creatinine biosensor comprising at least a pair of a working electrode and a counter electrode on a substrate, wherein a reagent solution is dried on the electrodes or on the substrate near the electrodes to immobilize the reagent. The reagent solution is prepared by dissolving creatininase, creatinase, sarcosine oxidase, and potassium ferricyanide (mediator) in a buffer solution of pH 7 to 8.5. It is also disclosed that a buffer solution pH of less than 7 or greater than 8.5 is not preferable since the enzyme activity decreases.

PTL 7 discloses quantifying creatinine by colorimetry or an electrochemical detection method using sarcosine oxidase and a mediator encapsulated in cyclodextrin. Specifically, PTL 7 cites α-naphthoquinone (1,4-naphthoquinone) as an example of a mediator encapsulated in cyclodextrin, but discloses that mediators are not suitable for the enzymatic quantification of creatinine if they are not encapsulated in cyclodextrin.

Also, still another enzymatic method is a method of spectroscopically quantifying creatinine by carrying out the reactions of formulas (1) and (2) and additionally carrying out the reaction between sarcosine and a tetrazolium indicator instead of the reaction of formula (3) (see, for example, PTL 8). PTL 8 discloses that the reagent composition for creatinine quantification comprises a reagent mixture composed of creatinine hydrolase, creatine amidinohydrolase, sarcosine dehydrogenase, thiazolyl blue serving as the tetrazolium indicator, and potassium phosphate of pH 7.5.

Also, still another enzymatic method is a method of converting creatinine to glycine and formaldehyde by use of creatinine amidohydrolase, creatine amidinohydrolase, and sarcosine dehydrogenase, causing the produced formaldehyde to give a color with the aid of a color reagent, and quantifying creatinine from the absorbance (see, for example, PTL 9). PTL 9 discloses using a phosphate buffer solution of pH 7.5 and potassium ferricyanide serving as a reaction accelerator for promoting the formation of formaldehyde in addition to creatinine amidohydrolase, creatine amidinohydrolase, sarcosine dehydrogenase, and the color reagent.

Also, still another enzymatic method is a method of quantifying creatinine using an electrode on which a polymer that catalyzes the hydrolysis of creatinine, sarcosine oxidase, and a mediator are immobilized (see, for example, PTL 10). PTL 10 discloses using, for example, potassium ferricyanide, ferrocene, an osmium derivative, or phenazine methosulfate (PMS) as the mediator.

Still another creatinine quantification method is a method using 1,4-naphthoquinone-2-potassium sulfonate (see, for example, PTL 11 and NPLs 1 to 3).

CITATION LIST

Patent Literature

PTL 1: U.S. Pat. No. 3,705,013
PTL 2: Japanese Laid-Open Patent Publication No. 2001-512692

PTL 3: Japanese Laid-Open Patent Publication No. Sho 62-257400
PTL 4: Japanese Laid-Open Patent Publication No. 2003-533679
PTL 5: U.S. Pat. No. 5,466,575
PTL 6: Japanese Laid-Open Patent Publication No. 2006-349412
PTL 7: Japanese Laid-Open Patent Publication No. 2005-118014
PTL 8: Japanese Laid-Open Patent Publication No. Sho 55-023998
PTL 9: Japanese Laid-Open Patent Publication No. Sho 54-151095
PTL 10: Japanese Laid-Open Patent Publication No. 2003-326172
PTL 11: Japanese Laid-Open Patent Publication No. Sho 63-033661

Non Patent Literature

NPL 1: Sullivan et al., "A Highly Specific Test for Creatinine", Journal of Biological Chemistry, 1958, Vol. 233, No. 2, p. 530-534
NPL 2: Narayanan et al., "Creatinine: A Review", Clinical Chemistry, 1980, Vol. 26, No. 8, p. 1119-1126
NPL 3: Cooper et al., "An Evaluation of Four Methods of Measuring Urinary Creatinine", 1961, Vol. 7, No. 6, P. 665-673

SUMMARY OF INVENTION

Technical Problem

However, the above-described conventional methods have the following problems.

In the method described in PTL 1, due to the influence of interferents such as amino acids including glycine, histidine, glutamine, and serine, proteins, sugars such as glucose, acetone, and bilirubin, it is difficult to accurately quantify creatinine in samples containing such substances, for example, in biological samples such as urine and blood. For example, amino acids and sugars such as glucose undesirably react with picric acid.

Also, in the method described in PTL 2, it is difficult to accurately quantify creatinine since the change in pH or potential is unstable.

Also, in the methods described in PTLs 2 to 10, if a sample contains an ion species such as salt or urea, the enzyme activity decreases due to enzyme denaturation. Thus, the reaction speed varies with the concentration of the ion species or urea contained in the sample. Therefore, in the quantification of creatinine in a sample containing an ion species or urea, for example, a biological sample such as urine or blood, the measurement result involves an error depending on the concentration of the ion species or urea contained in the sample.

Further, with respect to the methods of PTL 11 and NPL 1 using 1,4-naphthoquinone-2-potassium sulfonate, NPLs 2 and 3 have reported that the reproducibility of the results measured by these methods is very low.

In view of the above-described problems associated with conventional art, it is therefore a first object of the invention to provide a creatinine concentration measuring method, device and apparatus capable of quantifying creatinine contained in a sample with good accuracy and good reproducibility.

It is a second object of the invention to provide a salt measuring method, device and apparatus capable of quantifying the amount of salt contained in urine with good accuracy and good reproducibility.

Solution to Problem

In order to solve the above-noted problems with conventional art, the method for measuring the concentration of creatinine according to the invention includes the steps of:

(A) mixing a sample containing creatinine with a creatinine quantitative reagent containing a metal complex of at least one of hexacyanoferrate and hexacyanoruthenate in the absence of picric acid and any enzyme responsive to creatinine, to cause the creatinine to reduce the metal complex;

(B) electrochemically or optically measuring the amount of the metal complex reduced in the step (A); and (C) determining the concentration of the creatinine contained in the sample from the amount of the reduced metal complex measured in the step (B).

The method for measuring the amount of salt according to the invention includes the steps of:

(a) mixing urine, which is a sample, with a creatinine quantitative reagent containing a metal complex of at least one of hexacyanoferrate and hexacyanoruthenate in the absence of picric acid and any enzyme responsive to creatinine, to cause creatinine contained in the urine to reduce the metal complex;

(b) electrochemically or optically measuring the amount of the metal complex reduced in the step (a);

(c) measuring an electrical property of the urine; and (d) determining a value reflecting the amount of salt excreted in the urine from the amount of the reduced metal complex measured in the step (b) and the electrical property measured in the step (c).

It is preferable to perform the step (c) before the step (a), or after the step (b) and before the step (d).

In the step (A) and step (a), the pH of the sample after the mixing is preferably set to 2.5 or more and 7 or less, and more preferably set to 3 or more and 6 or less. In the step (A) and step (a), the sample is preferably mixed with a phosphate buffer; in this case, it is particularly preferable to adjust the pH of the sample to 5 to 6. In the step (A) and step (a), if the sample is mixed with a cationic hydrophilic polymer, the reproducibility of the reaction between creatinine and the reagent improves. The cationic hydrophilic polymer is preferably cationic guar gum.

The device for measuring the concentration of creatinine according to the invention is a device used in the above-mentioned method for measuring the concentration of creatinine. This device comprises:

a sample holding space for holding a sample containing creatinine in the absence of picric acid and any enzyme responsive to creatinine;

a sample inlet for introducing the sample into the sample holding space, the sample inlet communicating with the sample holding space;

a creatinine quantitative reagent disposed in the sample holding space, the creatinine quantitative reagent containing a metal complex of at least one of hexacyanoferrate and hexacyanoruthenate; and two or more electrodes disposed in the sample holding space or an optical measurement window disposed on the sample holding space.

Also, the device for measuring the amount of salt according to the invention is a device used in the above-mentioned method for measuring the amount of salt. This device comprises:

a first sample holding space for holding urine, which is a sample, in the absence of picric acid and any enzyme responsive to creatinine;

a first sample inlet for introducing the urine into the first sample holding space, the first sample inlet communicating with the first sample holding space;

a creatinine quantitative reagent disposed in the first sample holding space, the creatinine quantitative reagent containing a metal complex of at least one of hexacyanoferrate and hexacyanoruthenate;

two or more electrodes disposed in the first sample holding space or an optical measurement window disposed on the first sample holding space, a second sample holding space for holding the urine;

a second sample inlet for introducing the urine into the second sample holding space, the second sample inlet communicating with the second sample holding space; and two or more electrodes disposed in the second sample holding space.

The apparatus for measuring the concentration of creatinine according to the invention comprises:

a measuring device mounting port for mounting the above-mentioned device for measuring the concentration of creatinine;

a measurement system for electrochemically or optically measuring the amount of the metal complex reduced by the creatinine in the sample holding space of the measuring device; and an arithmetic unit for determining the concentration of the creatinine contained in the sample from the amount of the reduced metal complex measured by the measurement system.

The apparatus for measuring the amount of salt according to the invention comprises:

a measuring device mounting port for mounting the above-mentioned device for measuring the amount of salt;

a first measurement system for electrochemically or optically measuring the amount of the metal complex reduced by the creatinine in the first sample holding space of the measuring device;

a second measurement system for measuring an electrical property of the urine in the second sample holding space of the measuring device; and an arithmetic unit for determining a value reflecting the amount of salt excreted in the urine from the amount of the reduced metal complex measured by the first measurement system and the electrical property measured by the second measurement system.

Advantageous Effects of Invention

According to the method for measuring the concentration of creatinine of the invention, creatinine contained in a sample is quantified with good accuracy in the absence of picric acid and any enzyme responsive to creatinine.

BRIEF DESCRIPTION OF DRAWINGS

FIG. 2 is a perspective view showing the appearance of an apparatus for measuring creatinine concentration in the same embodiment;

FIG. 11 is a graph showing the relationship between the creatinine concentration in samples and the current value measured in Example 1 of the invention;

FIG. 12 is a graph showing the relationship between the potential applied to the first electrode and the current value measured in Example 4 of the invention;

FIG. 13 is a graph showing the relationship between the creatinine concentration in samples and the current value measured in the same Example;

FIG. 14 is a graph showing the relationship between the creatinine concentration in samples and the current value measured in the Example 5 of the invention; and FIG. 15 is a graph showing variation in the current value measured with creatinine concentration measuring devices of the same Example and a Reference Example.

DESCRIPTION OF EMBODIMENTS

Figure 1:
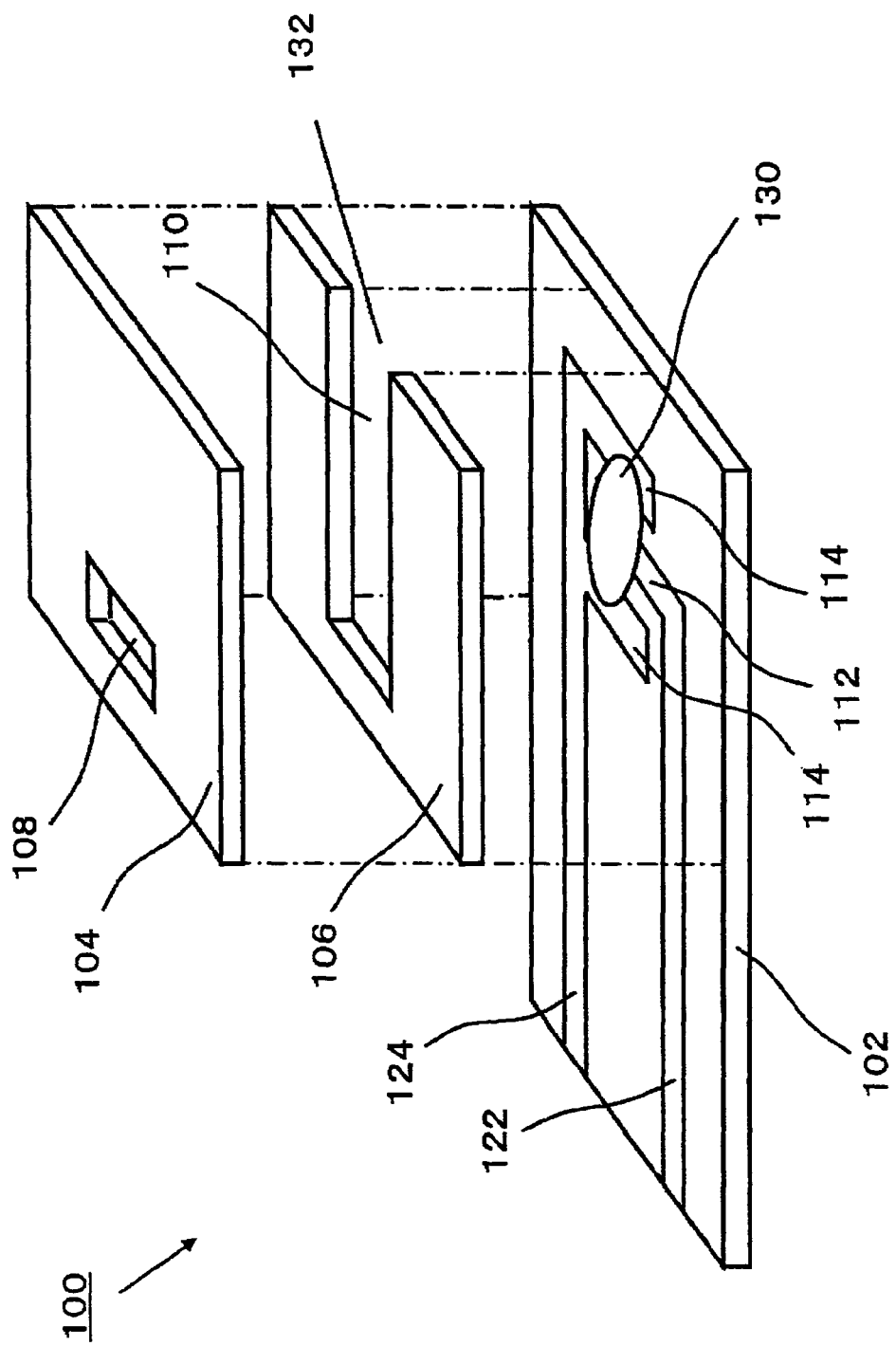
FIG. 1 is an exploded perspective view showing the structure of a device for measuring creatinine concentration in Embodiment 1 of the invention.

The inventors have found that creatinine directly reacts with hexacyanoferrate (III) (trivial name: ferricyanide), which is a trivalent anion represented by the following formula (4). In this reaction, in the absence of picric acid and any enzyme responsive to creatinine (e.g., creatinine amidohydrolase, creatinine deiminase), creatinine reacts with trivalent hexacyanoferrate to form an oxidation product of creatinine and hexacyanoferrate (II) (trivial name: ferrocyanide), which is a tetravalent anion represented by the following formula (5). The inventors have found as a result of analyses that methylguanidine and N-methyluric acid are formed as reaction products. Therefore, the oxidation product of creatinine produced in this reaction is estimated to be creatol.

$$[Fe(CN)_6]^{3-} \tag{4}$$

$$[Fe(CN)_6]^{4-} \tag{5}$$

Also, the inventors have found that creatinine directly reacts with hexacyanoruthenate (III), which is a trivalent anion represented by the following formula (6). In this reaction, in the absence of picric acid and any enzyme responsive to creatinine, creatinine reacts with trivalent anion hexacyanoruthenate to form an oxidation product of creatinine and hexacyanoruthenate (II), which is a tetravalent anion represented by the following formula (7).

$$[\text{Ru(CN)}_6]^{3-} \quad (6)$$

$$[\text{Ru(CN)}_6]^{4-} \quad (7)$$

The invention is based on the above-noted findings and characterized in that at least one of hexacyanoferrate and hexacyanoruthenate is used as a reagent for the measurement of creatinine concentration.

Hexacyanoferrate and hexacyanoruthenate are usually present in the form of a complex salt. For example, in the state of a solid, hexacyanoferrate or hexacyanoruthenate forms a complex salt with a counter cation. In a solution, a complex salt of hexacyanoferrate or hexacyanoruthenate is ionized, and hexacyanoferrate or hexacyanoruthenate is present in the form of a solvated anion.

The speed of the reaction between creatinine and a reagent, in particular, creatinine and trivalent hexacyanoferrate, is accelerated in the presence of a phosphate buffer. Also, when creatinine is reacted with a reagent in the presence of a phosphate buffer, the presence of a cationic hydrophilic polymer enhances the reproducibility of the reaction.

The method for measuring the concentration of creatinine according to the invention includes:

(A) mixing a sample containing creatinine with a creatinine quantitative reagent containing a metal complex of at least one of hexacyanoferrate and hexacyanoruthenate in the absence of picric acid and any enzyme responsive to creatinine, to cause the creatinine to reduce the metal complex;

(B) electrochemically or optically measuring the amount of the metal complex reduced in the step (A); and (C) determining the concentration of the creatinine contained in the sample from the amount of the reduced metal complex measured in the step (B).

According to this method, unlike conventional measuring methods, creatinine directly reacts with the metal complex contained in the creatinine quantitative reagent in the absence of picric acid and any enzyme responsive to creatinine. Therefore, the reaction proceeds without being affected by interferents including ion species such as salt, urea, proteins, amino acids, sugars, acetone, and bilirubin. Hence, even when a biological sample such as urine or blood is used, it is possible to quantify creatinine contained in the sample with better accuracy than conventional measuring methods.

The creatinine quantitative reagent is preferably hexacyanoferrate. Hexacyanoferrate is chemically stable, and reacts with creatinine efficiently. Examples of usable complex salts of hexacyanoferrate include potassium ferricyanide and sodium ferricyanide.

Hexacyanoferrate may be, before being reacted with creatinine, trivalent hexacyanoferrate, i.e., an oxidized form of hexacyanoferrate, or may be tetravalent hexacyanoferrate, i.e., a reduced form of hexacyanoferrate. When the creatinine quantitative reagent is tetravalent hexacyanoferrate, the tetravalent hexacyanoferrate dissolved in a sample is oxidized to trivalence as appropriate. Trivalent hexacyanoferrate is obtained, for example, by oxidizing tetravalent hexacyanoferrate on an electrode.

The creatinine quantitative reagent may be hexacyanoruthenate. Examples of usable complex salts of hexacyanoruthenate include potassium hexacyanoruthenate and sodium hexacyanoruthenate.

Hexacyanoruthenate may be, before being reacted with creatinine, trivalent hexacyanoruthenate, i.e., an oxidized form of hexacyanoruthenate, or may be tetravalent hexacyanoruthenate, i.e., a reduced form of hexacyanoruthenate. When the creatinine quantitative reagent is tetravalent hexacyanoruthenate, the tetravalent hexacyanoruthenate dissolved in a sample is oxidized to trivalence as appropriate. Trivalent hexacyanoruthenate is obtained, for example, by oxidizing tetravalent hexacyanoruthenate on an electrode.

In the step A, the sample may be further mixed with a buffer.

Examples of buffers include phosphate buffers such as dipotassium hydrogen phosphate and potassium dihydrogen phosphate, citrate buffers, phthalate buffers, acetate buffers, an MES (2-Morpholinoethane sulfonic acid) buffer. It is preferable to mix such a buffer with the sample so that the pH of the sample is adjusted to 3 to 6. It is particularly preferable to mix a phosphate buffer with the sample so that the pH of the sample is adjusted to 5 to 6.

When the creatinine quantitative reagent is hexacyanoferrate, it is particularly preferable to mix a phosphate buffer with the sample so that the pH of the sample is adjusted to 5 to 6. This increases the speed of the direct reaction between creatinine and trivalent hexacyanoferrate, thereby allowing a reduction in measurement time.

The phosphate buffer is preferably composed of dipotassium hydrogen phosphate and potassium dihydrogen phosphate. By dissolving these phosphates in the sample, the pH of the sample is readily adjusted to the range of 5 to 6.

The concentration of the phosphate buffer (concentration of phosphorus atoms) in the sample is preferably 5 to 1100 mM, and more preferably 5 to 500 mM. The inventors have found that as the concentration of the phosphate ion increases, the speed of the reaction between creatinine and trivalent hexacyanoferrate increases. If the concentration of the phosphate buffer is 5 mM or more, a sufficient reaction speed is obtained. Also, 1100 mM is the upper limit of the solubility of the phosphate buffer.

In the step A, the sample may be mixed with a cationic hydrophilic polymer in addition to the buffer. Hexacyanoferrate, hexacyanoruthenate, and the phosphate buffer are anionic. Thus, the reagent is thought to be electrostatically drawn by the cationic group of the cationic hydrophilic polymer so that the reagent becomes uniform. Probably for this reason, creatinine contained in a sample is quantified with good reproducibility.

The concentration of the cationic hydrophilic polymer in the sample is preferably 0.02 to 0.5% by weight. If the concentration of the cationic hydrophilic polymer is 0.02% by weight or more, reproducibility is improved sufficiently. Also, if the concentration of the cationic hydrophilic polymer is 0.5% by weight or less, the cationic hydrophilic polymer is sufficiently dissolved in a sample.

An example of cationic hydrophilic polymers is cationic guar gum. Guar gum is a polysaccharide derived from the endosperm of seeds of guar, which is a leguminous plant. Cationic guar gum is a cationized form of guar gum. An example of cationic guar gum used in the invention is guar hydroxypropyltrimonium chloride.

In the method for measuring the concentration of creatinine according to the invention, it is most preferable to mix a phosphate buffer and a cationic hydrophilic polymer to a sample so that the pH of the sample is adjusted to the range of 5 to 6.

When the amount of the reduced metal complex is electrochemically measured, for example, the step (B) comprises:

(D) bringing the sample into contact with two or more electrodes and applying a voltage between the two electrodes; and (E) detecting the current value or the amount of electric charge flowing between the two electrodes.

Also, the step (C) comprises the step of determining the concentration of creatinine contained in the sample from the current value or the amount of electric charge detected in the step (E).

In this case, the concentration of creatinine contained in a sample is electrochemically determined with ease.

When the amount of the reduced metal complex is optically measured, for example, the step (B) comprises the steps of:

(F) irradiating the sample with light; and (G) detecting the light transmitted through the sample or the light reflected by the sample.

Also, the step (C) comprises the step of determining the concentration of creatinine contained in the sample from the intensity of the transmitted light or the reflected light detected in the step (G).

In this case, the concentration of creatinine contained in a sample is optically determined with ease.

The method for measuring the amount of salt according to the invention uses urine as a sample, and comprises the following steps (c) and (d) in addition to the steps (A) and (B) of the above-mentioned method for measuring creatinine concentration.

That is, the method for measuring the amount of salt according to the invention comprises the steps of:

(a) mixing urine, which is a sample, with a creatinine quantitative reagent containing a metal complex of at least one of hexacyanoferrate and hexacyanoruthenate in the absence of picric acid and any enzyme responsive to creatinine, to cause creatinine contained in the urine to reduce the metal complex;

(b) electrochemically or optically measuring the amount of the metal complex reduced in the step (a);

(c) measuring an electrical property of the urine; and (d) determining a value reflecting the amount of salt excreted in the urine from the amount of the reduced metal complex measured in the step (b) and the electrical property measured in the step (c).

An electrical property of urine in which no creatinine quantitative reagent is dissolved reflects the concentration of electrolyte contained in the urine. The concentration of electrolyte contained in the urine correlates with the concentration of salt contained in the urine. Components such as salt are affected by water intake, sweating, and the like, so they are concentrated or diluted before being excreted in the urine. Thus, the concentration of urinary components such as salt in a random urine sample, which is a urine sample collected randomly irrespective of daytime or nighttime, fluctuates due to the influence of concentration and dilution of urine.

On the other hand, the amount of creatinine produced is dependent on the amount of muscle, as described above. It is thus known that the amount of urinary creatinine excretion per unit time is constant. Even in the case of using a random urine sample, the influence of the concentration and dilution of urine is corrected, for example, by obtaining the ratio of the concentration of a measured urinary component to the creatinine concentration (the ratio of urinary component/creatinine).

The method for measuring the amount of salt according to the invention uses the value measured in the step (b), which reflects the creatinine concentration with high accuracy and good reproducibility, and the electrical property measured in the step (c), which reflects the salt concentration. As a result, the influence of the concentration and dilution of urine is corrected with high accuracy and good reproducibility. It is therefore possible to obtain a value that properly reflects the amount of urinary salt excretion.

Examples of electrical properties of urine include resistance, conductivity, impedance, voltage (or current) signal produced in response to input current (or voltage) signal, and phase difference between the phase of input AC signal and the phase of output AC signal.

Examples of values reflecting the amount of urinary salt excretion determined in the step (d) include the amount of salt per unit amount of creatinine, the amount of urinary salt excretion per unit time (e.g., 1 day), and the amount of salt intake per unit time (e.g., 1 day).

The device for measuring the concentration of creatinine according to the invention comprises:

a sample holding space for holding a sample containing creatinine in the absence of picric acid and any enzyme responsive to creatinine;

a sample inlet for introducing the sample into the sample holding space, the sample inlet communicating with the sample holding space; and a creatinine quantitative reagent disposed in the sample holding space, the creatinine quantitative reagent containing a metal complex of at least one of hexacyanoferrate and hexacyanoruthenate. This device is used in the above-mentioned method for measuring the concentration of creatinine.

With this device, creatinine directly reacts with the metal complex contained in the reagent in the sample holding space in the absence of picric acid and any enzyme responsive to creatinine, unlike conventional measuring devices. Therefore, the reaction proceeds without being affected by interferents including ion species such as salt, urea, proteins, amino acids, sugars, acetone, and bilirubin. Hence, even in the case of using a biological sample such as urine or blood, it is possible to quantify creatinine contained in the sample with better accuracy than conventional measuring devices. Also, hexacyanoferrate, hexacyanoruthenate, and a phosphate buffer are anionic. Thus, they are thought to be electrostatically drawn by the cationic group of the cationic hydrophilic polymer so that the reagent becomes uniform. Probably for this reason, creatinine contained in a sample is quantified with good reproducibility.

The device for measuring the concentration of creatinine may include a phosphate buffer in the sample holding space, or may further include a cationic hydrophilic polymer.

The device for measuring the concentration of creatinine may include two or more electrodes in the sample holding space, or an optical measurement window disposed on the sample holding space.

In this case, the concentration of creatinine contained in a sample is electrochemically or optically determined with ease.

The device for measuring the amount of salt according to the invention comprises:

a first sample holding space for holding urine, which is a sample, in the absence of picric acid and any enzyme responsive to creatinine;

a first sample inlet for introducing the urine into the first sample holding space, the first sample inlet communicating with the first sample holding space;

a creatinine quantitative reagent disposed in the first sample holding space, the creatinine quantitative reagent containing a metal complex of at least one of hexacyanoferrate and hexacyanoruthenate;

a second sample holding space for holding the urine;

a second sample inlet for introducing the urine into the second sample holding space, the second sample inlet communicating with the second sample holding space; and two or more electrodes disposed in the second sample holding space. This device is used in the above-mentioned method for measuring the amount of salt.

This device can efficiently measure the amount of reduced metal complex, which accurately reflects the concentration of creatinine, and an electrical property of urine, which reflects the concentration of salt. By using the amount of reduced metal complex and the electrical property, the influence of concentration and dilution of urine is corrected with good accuracy. It is thus possible to obtain a value which properly reflects the amount of urinary salt excretion.

The device for measuring the amount of salt may further include two or more electrodes in the first sample holding space, or an optical measurement window disposed on the sample holding space.

The apparatus for measuring the concentration of creatinine according to the invention comprises:

a measuring device mounting port for mounting the above-mentioned device for measuring the concentration of creatinine;

a measurement system for electrochemically or optically measuring the amount of the metal complex reduced by the creatinine in the sample holding space of the measuring device; and an arithmetic unit for determining the concentration of the creatinine contained in the sample from the amount of the reduced reagent measured by the measurement system.

This measuring apparatus can electrochemically or optically measure the concentration of creatinine contained in a sample by using the above-mentioned device for measuring the concentration of creatinine.

When the concentration of creatinine contained in a sample is optically measured, the measurement system includes, for example, a light source for emitting light to the sample holding space of the measuring device, and a light receiver for detecting the light transmitted through the sample holding space or the light reflected in the sample holding space. Also, the arithmetic unit determines the concentration of the creatinine contained in the sample from the intensity of the transmitted light or the reflected light detected by the light receiver.

When the device for measuring the concentration of creatinine further includes two or more electrodes in the sample holding space, the measurement system includes, for example, a voltage application unit for applying a voltage between the two electrodes, and a detector for detecting the current value or the amount of electric charge flowing between the two electrodes. Also, the arithmetic unit determines the concentration of the creatinine contained in the sample from the current value or the amount of electric charge detected by the detector.

The apparatus for measuring the amount of salt according to the invention comprises:

a measuring device mounting port for mounting the above-mentioned device for measuring the amount of salt;

a first measurement system for electrochemically or optically measuring the amount of the metal complex reduced by the creatinine in the first sample holding space of the measuring device;

a second measurement system for measuring an electrical property of the urine in the second sample holding space of the measuring device; and an arithmetic unit for determining a value reflecting the amount of salt excreted in the urine from the amount of the reduced metal complex measured by the first measurement system and the electrical property measured by the second measurement system.

This measuring apparatus can correct the thickness of urine based on the urinary creatinine concentration quantified with high accuracy and good reproducibility and the measured electrical property of the urine. It is therefore possible to determine the amount of urinary salt with high accuracy and good reproducibility.

Examples of samples include aqueous solutions and body fluids such as blood, blood serum, blood plasma, urine, interstitial fluid, lymph, and saliva. In particular, urine is a very effective sample for non-invasive, daily healthcare at home. Since the concentration of ion species and urea in these body fluids is relatively high, the invention is very effective.

Preferable electrode materials used in the invention include at least one of gold, platinum, palladium, alloys and mixtures thereof, and carbon. These materials are chemically and electrochemically stable, thus realizing stable measurements. As a third electrode, it is also possible to use an electrode with stable potential, for example, a reference electrode such as an Ag/AgCl or saturated calomel electrode, in combination with the above-mentioned two electrodes. If the potential of one of the two electrodes is regulated relative to the third electrode, the potential for measurement becomes stable, which is preferable. Also, as the other electrode of the two electrodes, for example, an Ag/AgCl or saturated calomel electrode is used.

In the measuring devices of the invention, it is preferable that the creatinine quantitative reagent be stored in a dry state and dissolved by a sample when the sample is introduced in the sample holding space.

In the measuring devices of the invention, it is preferable that the buffer and the cationic hydrophilic polymer be stored in a dry state and dissolved by a sample when the sample is introduced in the sample holding space.

For example, a porous carrier made of glass fibers, filter paper, or the like is impregnated with a solution containing a creatinine quantitative reagent, and dried to dispose the creatinine quantitative reagent on the carrier. The carrier is then disposed on a portion to come into contact with a sample. Also, a solution containing a creatinine quantitative reagent may be directly applied to a portion of a wall of a measuring device to come into contact with a sample, and dried to dispose the creatinine quantitative reagent thereon. The solution containing a creatinine quantitative reagent may include a buffer and a cationic hydrophilic polymer.

It is preferable that the above-described devices be detachably mounted in the measuring device mounting ports of the measuring apparatuses. Also, in the case of using biological liquids such as urine and blood, in particular, it is preferable for hygienic reasons that the measuring devices be disposable.

Embodiments of the invention are hereinafter described with reference to drawings.

Embodiment 1

A device 100 for measuring creatinine concentration according to Embodiment 1 of the invention is described with reference to FIG. 1. FIG. 1 is an exploded perspective view showing the structure of the measuring device 100.

The measuring device 100 is used in a method for electrochemically quantifying the concentration of creatinine contained in a sample. The measuring device 100 is composed of an insulating first substrate 102 and an insulating second substrate 104 with an air vent 108 which are combined so as to sandwich an insulating spacer 106 with a slit 110. The first substrate 102, the second substrate 104, and the spacer 106 are made of, for example, polyethylene terephthalate.

The first substrate 102 has a first electrode 112, a second electrode 114, a first lead 122 electrically connected to the first electrode 112, and a second lead 124 electrically connected to the second electrode 114. Formed on the first electrode 112 and the second electrode 114 is a reagent layer 130 containing a creatinine quantitative reagent. The dimensions of the first substrate 102 may be suitably set; for example, the width is approximately 7 mm, the length is approximately 30 mm, and the thickness is approximately 0.7 mm.

Next, the method for producing the measuring device 100 is described. In this embodiment, potassium ferricyanide, which is a complex salt of hexacyanoferrate, is used as the creatinine quantitative reagent.

First, palladium is sputtered onto the first substrate 102 with a resin mask of an electrode pattern thereon, to form the first electrode 112, the second electrode 114, the first lead 122, and the second lead 124. The first electrode 112 and the second electrode 114 are electrically connected to the terminals of an apparatus for measuring creatinine concentration, which will be described below, by the first lead 122 and the second lead 124, respectively.

Next, a given amount of an aqueous solution of potassium ferricyanide, potassium dihydrogen phosphate, and dipotassium hydrogen phosphate or an aqueous solution of potassium ferricyanide, cationic guar gum, potassium dihydrogen phosphate, and dipotassium hydrogen phosphate is dropped on the first electrode 112 and the second electrode 114 formed on the first substrate 102 with a microsyringe or the like. Thereafter, the first substrate 102 is left for drying in an environment at room temperature to approximately 30° C., to form the reagent layer 130.

The concentration and amount of the reagent-containing aqueous solution to be applied thereto are selected depending on the characteristics and size of the necessary device. For example, the concentration of the trivalent hexacyanoferrate in the reagent-containing aqueous solution is approximately 0.1 M, and the dropping amount of the aqueous solution is approximately 1.4 μL. Also, when the reagent containing aqueous solution contains cationic guar gum, the concentration of the cationic guar gum in the aqueous solution is approximately 0.25% by weight, and the dropping amount is approximately 1.4 μL.

The area of the region on which the reagent layer 130 is formed is suitably selected in view of the solubility of the reagent in the sample and the like, and the area is, for example, approximately 3 mm$^2$.

Next, the first substrate 102 with the electrodes and the reagent layer 130 formed thereon is combined with the spacer 106 and the second substrate 104. Adhesive is applied to the portions of the first substrate 102, the spacer 106, and the second substrate 104 to be bonded. They are laminated, pressed, and allowed to stand for bonding. Instead of this method, it is also possible to combine them without applying adhesive and then thermally or ultrasonically bond the bonding portions by using a commercially available welding machine.

When the first substrate 102, the spacer 106, and the second substrate 104 are combined, a space is formed by the slit 110 of the spacer 106 between the first substrate 102 and the second substrate 104, and this space serves as a sample holding space. Also, the opening of the slit 110 serves as a sample inlet 132.

Figure 3:
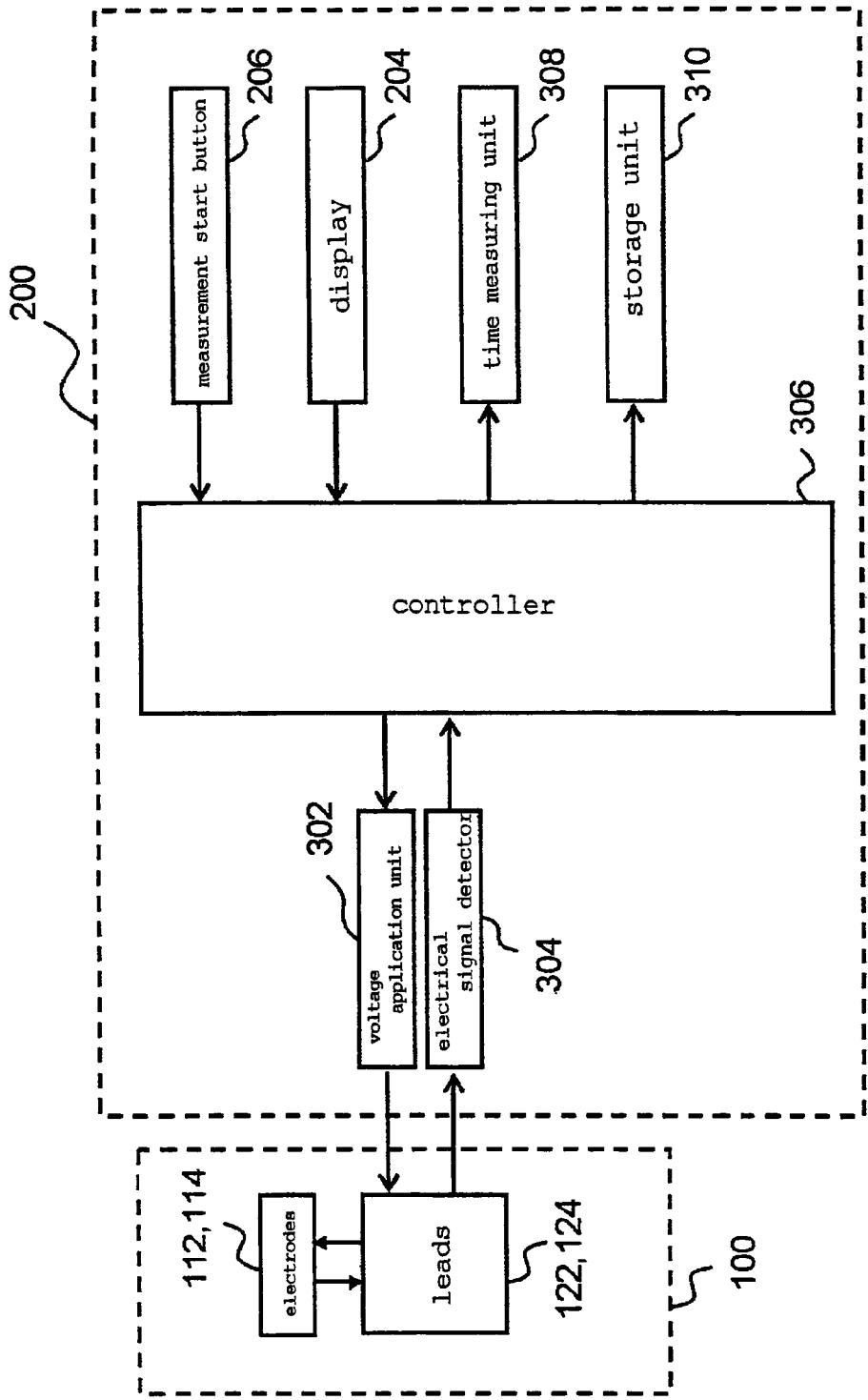
FIG. 3 is a block diagram showing the configuration of the apparatus for measuring creatinine concentration in the same embodiment.

Next, an apparatus 200 for measuring creatinine concentration according to this embodiment and the method for measuring creatinine concentration using this apparatus are described with reference to FIGS. 2 and 3. FIG. 2 is a perspective view showing the appearance of the measuring apparatus 200, and FIG. 3 is a block diagram showing the configuration of the measuring apparatus 200.

First, the structure of the measuring apparatus 200 is described with reference to FIG. 2.

A housing 202 of the measuring apparatus 200 has a measuring device mounting port 208 for mounting the measuring device 100, a display 204 for displaying measurement results etc., and a measurement start button 206 for starting the measurement of creatinine concentration by the measuring apparatus 200. Inside the measuring device mounting port 208 are a first terminal and a second terminal, which are to be electrically connected to the first lead 122 and the second lead 124 of the measuring device 100, respectively.

Next, the configuration inside the housing 202 of the measuring apparatus 200 is described with reference to FIG. 3.

The housing 202 of the measuring apparatus 200 contains a voltage application unit 302, an electrical signal detector 304, a controller 306, a time measuring unit 308, and a storage unit 310.

The voltage application unit 302 has the function of applying a voltage or potential to the first electrode 112 and the second electrode 114 of the measuring device 100 mounted in the measuring device mounting port 208. The voltage or potential is applied through the first terminal and the second terminal electrically connected to the first lead 122 and the second lead 124 of the measuring device 100, respectively.

The electrical signal detector 304 has the function of detecting the electrical signal from the first electrode 112 and the second electrode 114 through the first terminal and the second terminal. The electrical signal detector 304 corresponds to the detector of the invention.

The storage unit 310 stores correlation data corresponding to a calibration curve which indicates a correlation between creatinine concentrations and electrical signals detected by the electrical signal detector 304. Examples of the storage unit 310 include memory such as RAM and ROM.

The controller 306 has the function of converting the electrical signal detected by the electrical signal detector 304 to creatinine concentration by referring to the correlation data. The controller 306 corresponds to the arithmetic unit of the invention. Examples of the controller 306 include microcomputers such as a CPU (Central Processing Unit).

Next, the method for measuring creatinine concentration using the measuring device 100 and the measuring apparatus 200 according to this embodiment is described.

First, a user inserts the lead side of the measuring device 100 into the measuring device mounting port 208 of the measuring apparatus 200. As a result, the first lead 122 and the second lead 124 of the measuring device 100 come into contact with and are electrically connected to the first terminal and the second terminal inside the measuring device mounting port 208, respectively.

When the measuring device 100 is inserted into the measuring device mounting port 208, an insertion detecting controller 306. The insertion detecting switch comprises a microswitch installed in the measuring device mounting port 208. When the controller 306 detects the insertion of the measuring device 100 from the signal sent from the insertion detecting switch, the controller 306 controls the voltage application unit 302, so that a voltage (e.g., 0.2 V) is applied between the first electrode 112 and the second electrode 114 through the first terminal and the second terminal in order to detect the introduction of a sample.

Next, the user brings a sample into contact with the sample inlet 132 of the measuring device 100. Upon the contact, the sample (e.g., approximately 0.6 μL) is sucked into the sample holding space of the measuring device 100 from the sample inlet 132 by capillarity, so that the sample holding space is filled with the sample. When the sample comes into contact with the first electrode 112 and the second electrode 114, a current flows between the first electrode 112 and the second electrode 114 through the sample. The resultant change in electrical signal is detected by the electrical signal detector 304.

When the controller 306 detects the introduction of the sample into the sample holding space from the signal sent from the electrical signal detector 304, the controller 306 controls the voltage application unit 302, so that the voltage applied by the voltage application unit 302 is changed to a different voltage (e.g., 0 V or open circuit). Also, upon the detection of introduction of the sample, the controller 306 causes the time measuring unit 308, which is a timer, to start measuring time.

When the sample comes into contact with the reagent layer 130 exposed in the sample holding space, potassium ferricyanide contained in the reagent layer 130 dissolves in the sample. The dissolution of potassium ferricyanide in the sample produces trivalent hexacyanoferrate. The produced trivalent hexacyanoferrate directly reacts with creatinine contained in the sample to form an oxidation product of creatinine and tetravalent hexacyanoferrate.

When the controller 306 determines from the signal sent from the time measuring unit 308 that a predetermined time (e.g., 60 seconds) has passed, the controller 306 controls the voltage application unit 302, so that a voltage is applied between the first electrode 112 and the second electrode 114 in order to measure the concentration of tetravalent hexacyanoferrate. For example, a voltage is applied so as to make the first electrode 112 +0.5 to +0.6 V relative to the second electrode 114. After a certain time (e.g., five seconds) from the voltage application, an electrical signal such as the current flowing between the first electrode 112 and the second electrode 114 is measured by the electrical signal detector 304. At this time, the tetravalent hexacyanoferrate is oxidized at the first electrode 112. Therefore, the electrical signal measured by the electrical signal detector 304 is dependent on the creatinine concentration in the sample.

The controller 306 reads the correlation data which is stored in the storage unit 310 and which indicates a correlation between electrical signals and creatinine concentrations and refers to it. As a result, the electrical signal detected by the electrical signal detector 304 is converted to the creatinine concentration in the sample.

The creatinine concentration thus determined is displayed on the display 204. Upon the display of the creatinine concentration on the display 204, the user can recognize that the measurement of the creatinine concentration has been completed. It is preferred to store the creatinine concentration thus obtained in the storage unit 310 together with the time measured by the time measuring unit 308.

According to the measuring device 100, unlike conventional measuring devices, creatinine directly reacts with trivalent hexacyanoferrate in the sample holding space in the absence of picric acid and any enzyme responsive to creatinine. Therefore, the reaction proceeds without being affected by interferents including ion species such as salt, urea, proteins, amino acids, sugars, acetone, and bilirubin. Hence, even in the case of using a biological sample such as urine or blood, it is possible to quantify creatinine contained in the sample with better accuracy than conventional measuring devices. Also, since hexacyanoferrate and the phosphate buffer are anionic, they are thought to be electrostatically drawn by the cationic group of the cationic hydrophilic polymer to form a uniform reagent. Probably for this reason, creatinine contained in a sample is quantified with good reproducibility.

This embodiment has shown an example in which hexacyanoferrate is used as the creatinine quantitative reagent, but hexacyanoruthenate may also be used instead. When hexacyanoruthenate is used as the creatinine quantitative reagent, it is also possible to quantify creatinine contained in a sample with better accuracy than conventional measuring devices without being affected by interferents including ions species such as salt, urea, amino acids, and sugars.

This embodiment has shown an example in which the measuring device has one reagent layer, but this is not to be construed as limiting. The measuring device may have two reagent layers, for example, a first reagent layer containing a creatinine quantitative reagent and a second reagent layer containing a phosphate buffer.

This embodiment has shown an example in which when the controller detects the introduction of a sample into the sample holding space, the voltage applied by the voltage application unit is changed to a different voltage, but this is not to be construed as limiting. The voltage applied does not always need to be changed as long as a current dependent on the creatinine concentration is obtained. It is also possible to apply a voltage necessary for a measurement (e.g., such a voltage that the first electrode is +0.5 V to +0.6 V relative to the second electrode) from the detection of insertion of the measuring device and continue to apply that voltage after the detection of introduction of a sample.

This embodiment has shown an example in which the potential applied to the first electrode to obtain the electrical signal corresponding to the tetravalent hexacyanoferrate concentration is 0.5 to 0.6 V relative to the second electrode, but this is not to be construed as limiting. The voltage between the first electrode and the second electrode may be any voltage at which the metal complex included in the creatinine quantitative reagent and reduced in the redox reaction with creatinine (tetravalent hexacyanoferrate in this embodiment) is oxidized.

This embodiment has shown an example in which the time (reaction time) from the detection of introduction of a sample to the detection of an electrical signal is 60 seconds, but the time does not always need to be that value. The reaction time may be shorter than the above-mentioned time if the difference in current value corresponding to the difference in creatinine concentration is effectively detected. If the reaction time is made longer, the reaction between creatinine and trivalent anion hexacyanoferrate is more likely to reach a complete or steady state. Hence, the amount of creatinine is quantified more accurately without being affected by ambient conditions such as temperature.

This embodiment has shown an example in which an electrical signal is detected five seconds after the application of a potential to the electrodes, but this time is not to be construed as limiting. This time may be any time when the difference in electrical signal corresponding to the difference in creatinine concentration is effectively detected.

Also, the shape, number, layout, etc. of the electrode system, leads, and terminals are not to be construed as being limited to those of this embodiment. This also applies to the other embodiments.

This embodiment has shown an example in which the amount of reduced metal complex is measured, but the decreased amount of oxidized metal complex may be measured to indirectly obtain the amount of reduced metal complex.

In order to facilitate the introduction of a sample into the sample holding space of the measuring device, a lecithin layer may be formed by dissolving lecithin in toluene or another organic solvent to prepare a solution, applying the solution onto the inner wall of the second substrate, and drying it. With this structure, the sample amount is made constant with better reproducibility. It is thus possible to quantify creatinine contained in a sample with better accuracy.

The apparatus for measuring creatinine concentration may further include a recorder for recording measurement results in a storage medium such as an SD card. When measurement results are stored in a removable storage medium, the measurement results can be readily taken out of the measuring apparatus. It is thus easy to have the measurement results analyzed by an analytical laboratory.

The measuring apparatus may further include a transmitter for transmitting measurement results to outside of the measuring apparatus. In this case, the measurement results may be transmitted to an analytical department in a hospital, an analytical laboratory, or the like. Hence, the time from the measurement to the analysis is shortened.

The measuring apparatus may further include a receiver for receiving the results of analysis by an analytical department, an analytical laboratory, or the like. This permits prompt feedback of the analysis results to the user.

Embodiment 2

Figure 4:
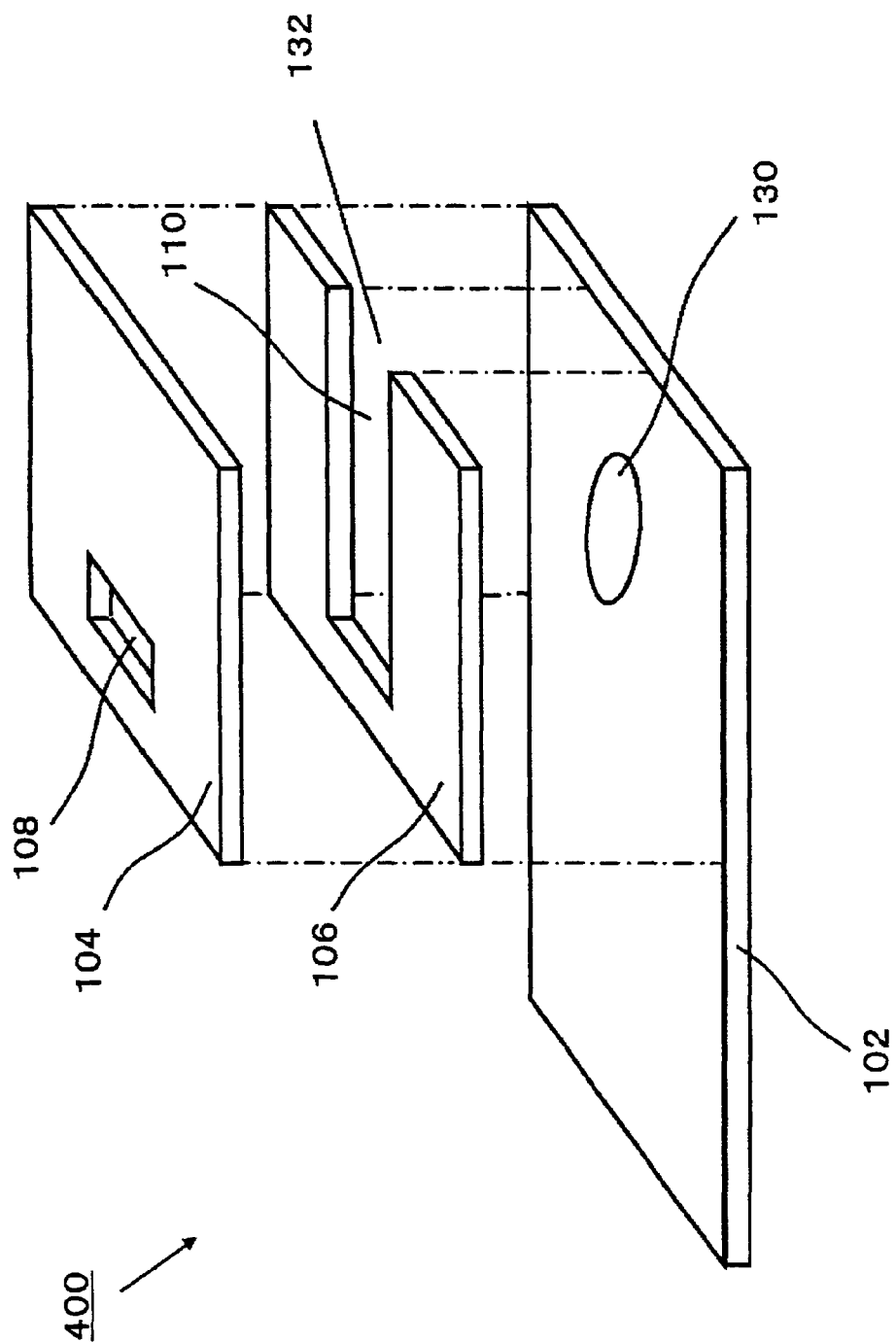
FIG. 4 is an exploded perspective view showing the structure of a device for measuring creatinine concentration in Embodiment 2 of the invention.

Next, a device 400 for measuring creatinine concentration according to Embodiment 2 of the invention is described with reference to FIG. 4. FIG. 4 is an exploded perspective view showing the structure of the measuring device 400.

The measuring device 400 is used in a method for optically quantifying the concentration of creatinine contained in a sample. The measuring device 400 is composed of a first substrate 102 and a second substrate 104 with an air vent 108 which are combined so as to sandwich a spacer 106 with a slit 110. The first substrate 102, the second substrate 104, and the spacer 106 are made of, for example, polyethylene terephthalate.

In the measuring device 400, unlike the measuring device 100 according to Embodiment 1, the first substrate 102 does not have a first electrode 112, a second electrode 114, a first lead 122, and a second lead 124. Also, a reagent layer 130 containing a creatinine quantitative reagent is disposed on the first substrate 102, not on the first electrode 112 and the second electrode 114.

Next, the method for producing the measuring device 400 is described.

First, a given amount of an aqueous solution containing a creatinine quantitative reagent, which is the same as that of Embodiment 1, is dropped on the first substrate 102 by using a microsyringe or the like. Thereafter, the first substrate 102 is left for drying in an environment at room temperature to approximately 30° C., to form the reagent layer 130. The concentration and amount of the reagent-containing aqueous solution to be applied thereto is selected depending on the characteristics and size of the necessary device; for example, they may be selected in the same manner as in Embodiment 1.

Next, the first substrate 102 with the reagent layer 130 formed thereon is combined with the spacer 106 and the second substrate 104. Adhesive is applied to the portions of the first substrate 102, the spacer 106, and the second substrate 104 to be bonded. They are laminated, pressed, and allowed to stand for bonding. Instead of this method, it is also possible to combine them without applying adhesive and then thermally or ultrasonically bond the bonding portions by using a commercially available welding machine.

When the first substrate 102, the spacer 106, and the second substrate 104 are combined, a space is formed by the slit 110 of the spacer 106 between the first substrate 102 and the second substrate 104, and this space serves as a sample holding space. Also, the opening of the slit 110 serves as a sample inlet 132.

Figure 5:
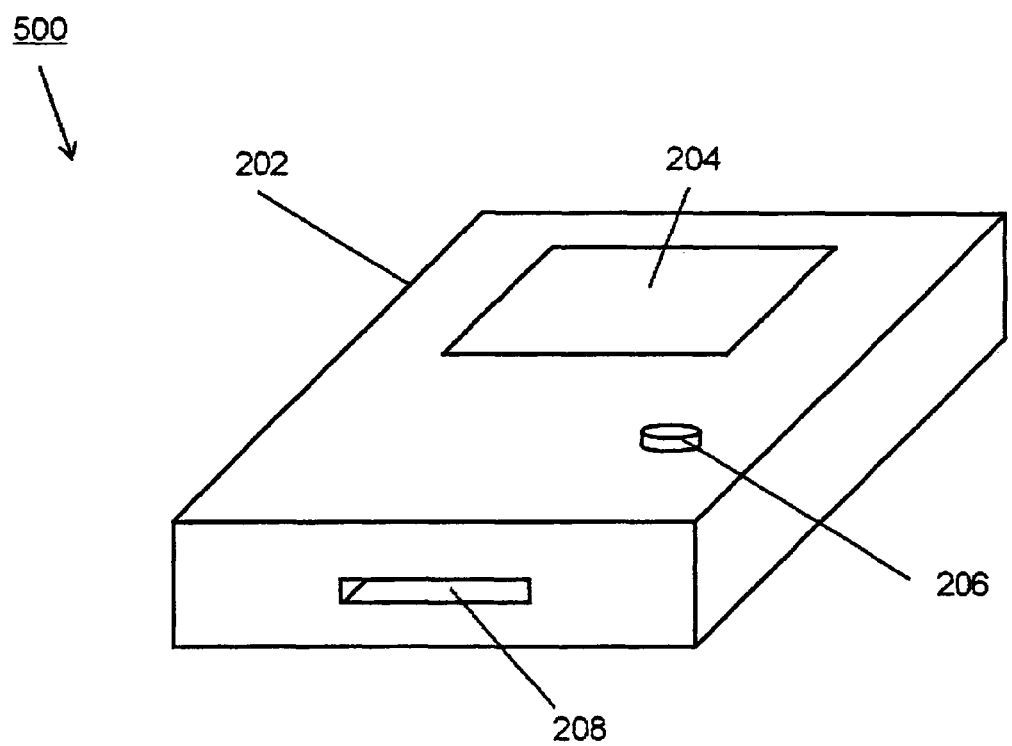
FIG. 5 is a perspective view showing the appearance of an apparatus for measuring creatinine concentration in the same embodiment.
Figure 6:
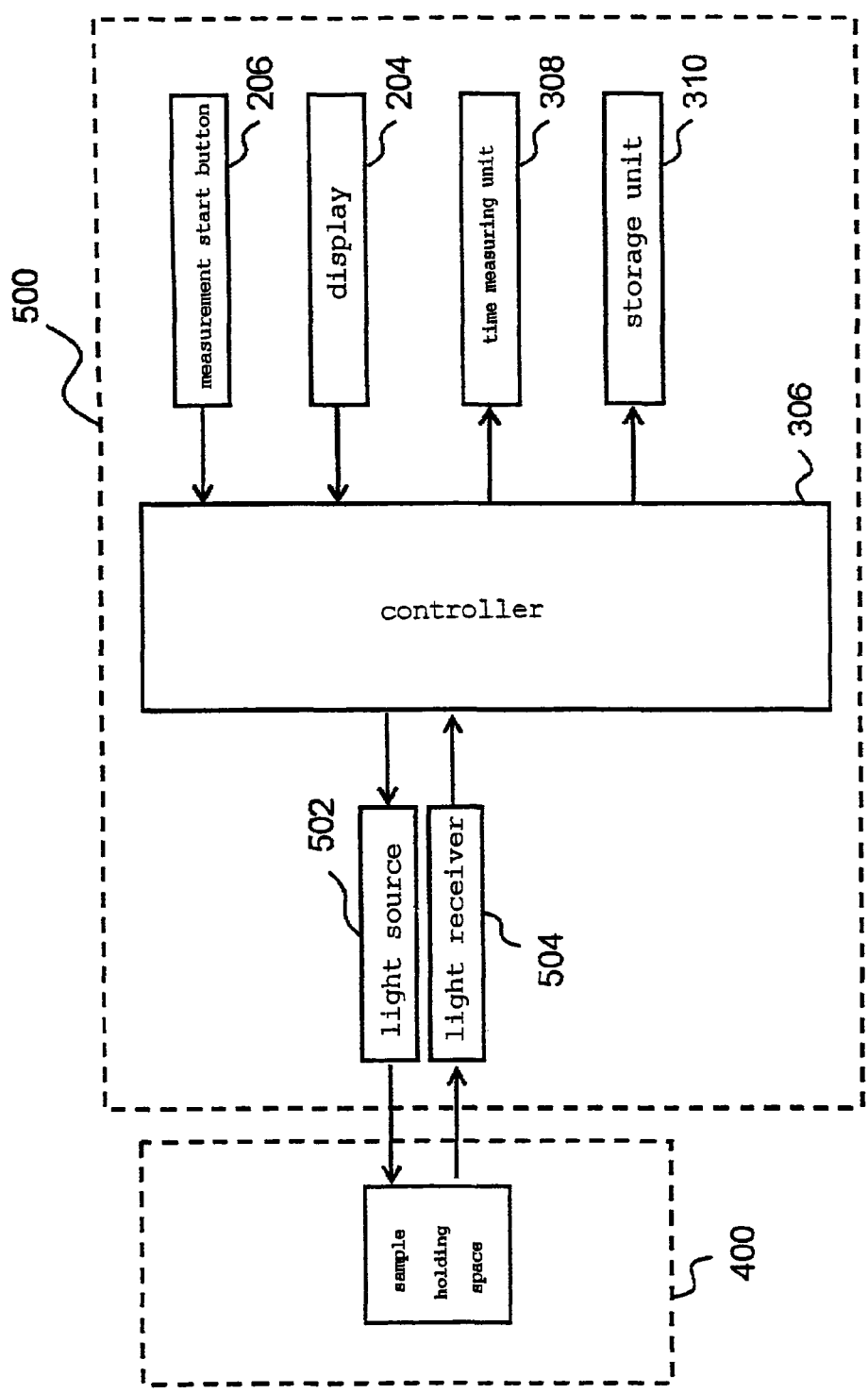
FIG. 6 is a block diagram showing the configuration of the apparatus for measuring creatinine concentration in the same embodiment.

Next, an apparatus 500 for measuring creatinine concentration according to this embodiment and the method for measuring creatinine concentration using this apparatus are described with reference to FIGS. 5 and 6. FIG. 5 is a perspective view showing the appearance of the measuring apparatus 500, and FIG. 6 is a block diagram showing the configuration of the measuring apparatus 500.

First, the structure of the measuring apparatus 500 is described with reference to FIG. 5.

A housing 202 of the measuring apparatus 500 has a measuring device mounting port 208 for mounting the measuring device 400, a display 204 for displaying measurement results etc., and a measurement start button 206 for starting the measurement of creatinine concentration by the measuring apparatus 500.

Next, the configuration inside the housing 202 of the measuring apparatus 500 is described with reference to FIG. 6.

The housing 202 of the measuring apparatus 500 contains a light source 502, a light receiver 504, a controller 306, a time measuring unit 308, and a storage unit 310.

The light source 502 has the function of emitting light to the sample holding space of the measuring device 400 mounted in the measuring device mounting port 208. The wavelength of the light emitted from the light source 502 is selected such that the absorption intensity changes depending on the reaction between creatinine and the metal complex in the creatinine quantitative reagent.

The light receiver 504 has the function of detecting the light emitted from the light source 502 and reflected in the sample holding space of the measuring device 400 mounted in the measuring device mounting port 208.

The storage unit 310 stores correlation data corresponding to a calibration curve which indicates a correlation between creatinine concentrations and reflected light intensities detected by the light receiver 504. Examples of the storage unit 310 include memory such as RAM and ROM.

The controller 306 has the function of converting the intensity of the reflected light detected by the light receiver 504 to creatinine concentration by referring to the correlation data. The controller 306 corresponds to the arithmetic unit of the invention. Examples of the controller 306 include microcomputers such as a CPU (Central Processing Unit).

Next, the method for measuring creatinine concentration using the measuring device 400 and the measuring apparatus 500 according to this embodiment is described.

First, a user inserts the other side of the measuring device 400 from the sample inlet 132 into the measuring device mounting port 208 of the measuring apparatus 500.

When the measuring device 400 is inserted into the measuring device mounting port 208, an insertion detecting switch is turned on, so that a signal is sent to the controller 306. The insertion detecting switch comprises a microswitch installed in the measuring device mounting port 208. When the controller 306 detects the insertion of the measuring device 400 from the signal sent from the insertion detecting switch, the controller 306 actuates the light source 502. As a result, light is emitted to the sample holding space of the measuring device 400 from the light source 502.

Next, the user brings a sample into contact with the sample inlet 132 of the measuring device 400. Upon the contact, the sample is sucked into the sample holding space of the measuring device 400 from the sample inlet 132 by capillarity, so that the sample holding space is filled with the sample. When the sample reaches the position of the sample holding space to which the light is emitted, the transmittance inside the sample holding space changes. The resulting change in the intensity of reflected light is detected by the light receiver 504.

When the controller 306 detects the introduction of the sample into the sample holding space from the signal sent from the light receiver 504, the controller 306 causes the time measuring unit 308, which is a timer, to start measuring time.

When the sample comes into contact with the reagent layer 130 exposed in the sample holding space, potassium ferricyanide contained in the reagent layer 130 dissolves in the sample. The dissolution of potassium ferricyanide in the sample produces trivalent hexacyanoferrate. The produced trivalent hexacyanoferrate directly reacts with creatinine contained in the sample to form an oxidation product of creatinine and tetravalent hexacyanoferrate. The change of the trivalent hexacyanoferrate to the tetravalent hexacyanoferrate causes a change in the absorption spectrum of the sample. The amount of change of the absorption spectrum of the sample is dependent on the concentration of the produced tetravalent hexacyanoferrate.

When the controller 306 determines from the signal sent from the time measuring unit 308 that a predetermined time (e.g., 60 seconds) has passed, it causes the light receiver 504 to measure the intensity of the light reflected in the sample holding space. The intensity of the reflected light measured by the light receiver 504 is dependent on the concentration of creatinine contained in the sample.

The controller 306 reads the correlation data which is stored in the storage unit 310 and which corresponds to a calibration curve indicating a correlation between creatinine concentrations and reflected light intensities detected by the light receiver 504, and refers to it. As a result, the intensity of the reflected light detected by the light receiver 504 is converted to the creatinine concentration in the sample.

The creatinine concentration thus determined is displayed on the display 204. Upon the display of the creatinine concentration on the display 204, the user can recognize that the measurement has been completed. It is preferred to store the creatinine concentration thus obtained in the storage unit 310 together with the time measured by the time measuring unit 308.

According to the measuring device 400, unlike conventional measuring devices, creatinine directly reacts with trivalent hexacyanoferrate in the sample holding space in the absence of picric acid and any enzyme responsive to creatinine. Therefore, the reaction proceeds without being affected by interferents including ion species such as salt, urea, proteins, amino acids, sugars, acetone, and bilirubin. Therefore, even in the case of using a biological sample such as urine or blood, it is possible to quantify creatinine contained in the sample with better accuracy than conventional measuring devices. Also, since hexacyanoferrate and the phosphate buffer are anionic, they are thought to be electrostatically drawn by the cationic group of the cationic hydrophilic polymer to form a uniform reagent. Probably for this reason, creatinine contained in a sample is quantified with good reproducibility.

In this embodiment, the measuring device may include two or more reagent layers in the same manner as in Embodiment 1.

This embodiment has shown an example in which the time (reaction time) from the detection of introduction of a sample to the detection of reflected light intensity is 60 seconds, but the time does not always need to be that value. The reaction time may be shorter than the above-mentioned time if the difference in reflected light intensity corresponding to the difference in creatinine concentration is effectively detected. If the reaction time is made longer, the amount of creatinine is determined more accurately.

In order to facilitate the introduction of a sample into the sample holding space, the measuring device may have a lecithin layer in the same manner as in Embodiment 1.

In the same manner as in Embodiment 1, the apparatus for measuring creatinine concentration may further include a recorder for recording measurement results in a storage medium such as an SD card. Also, the measuring apparatus may further include a transmitter for transmitting measurement results to outside of the measuring apparatus. Further, the measuring apparatus may further include a receiver for receiving the results of analysis by an analytical department, an analytical laboratory, or the like.

Embodiment 3

Figure 7:
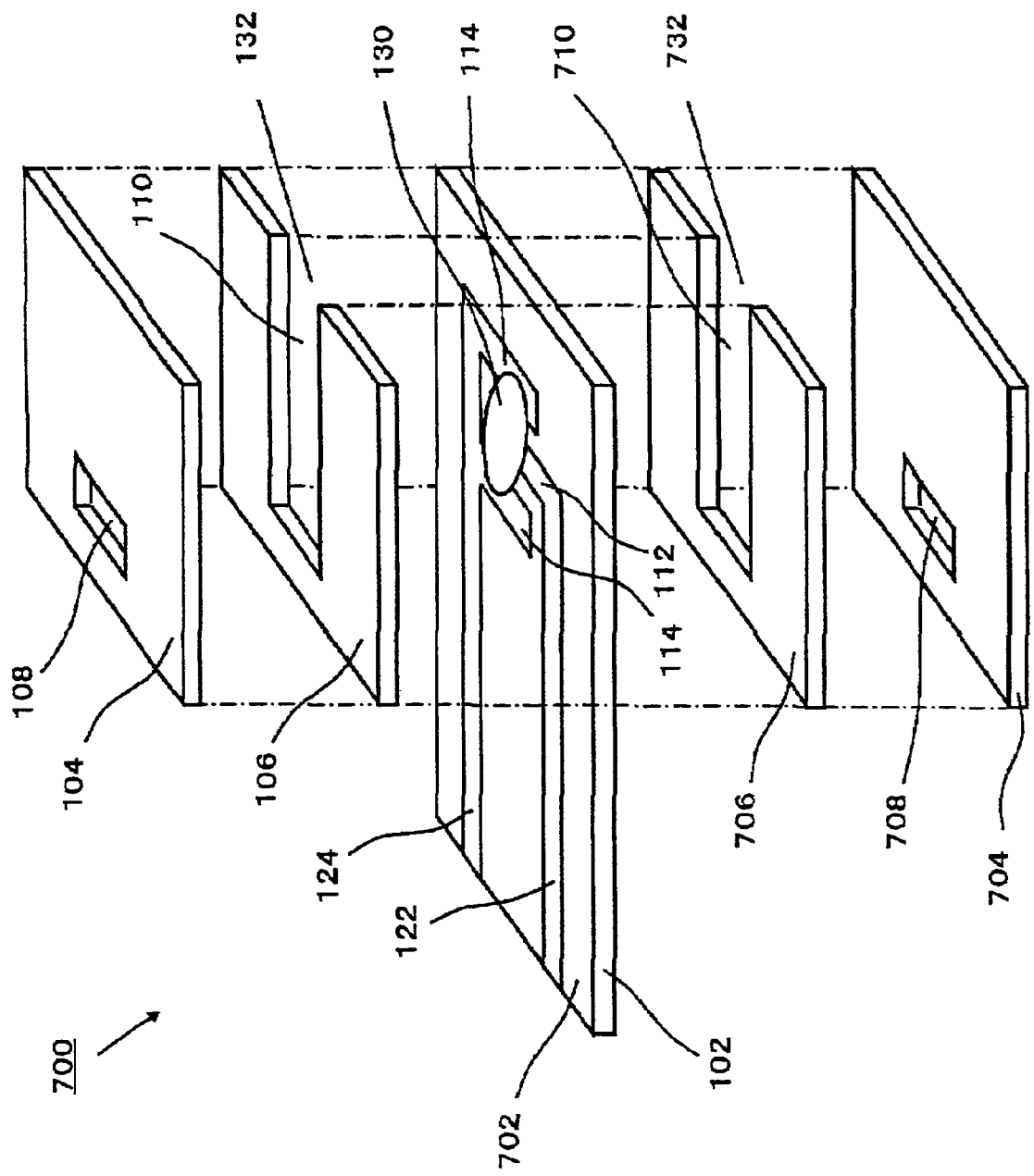
FIG. 7 is an exploded perspective view showing the structure of a device for measuring the amount of salt in Embodiment 3 of the invention seen from the first face side of the first substrate.
Figure 8:
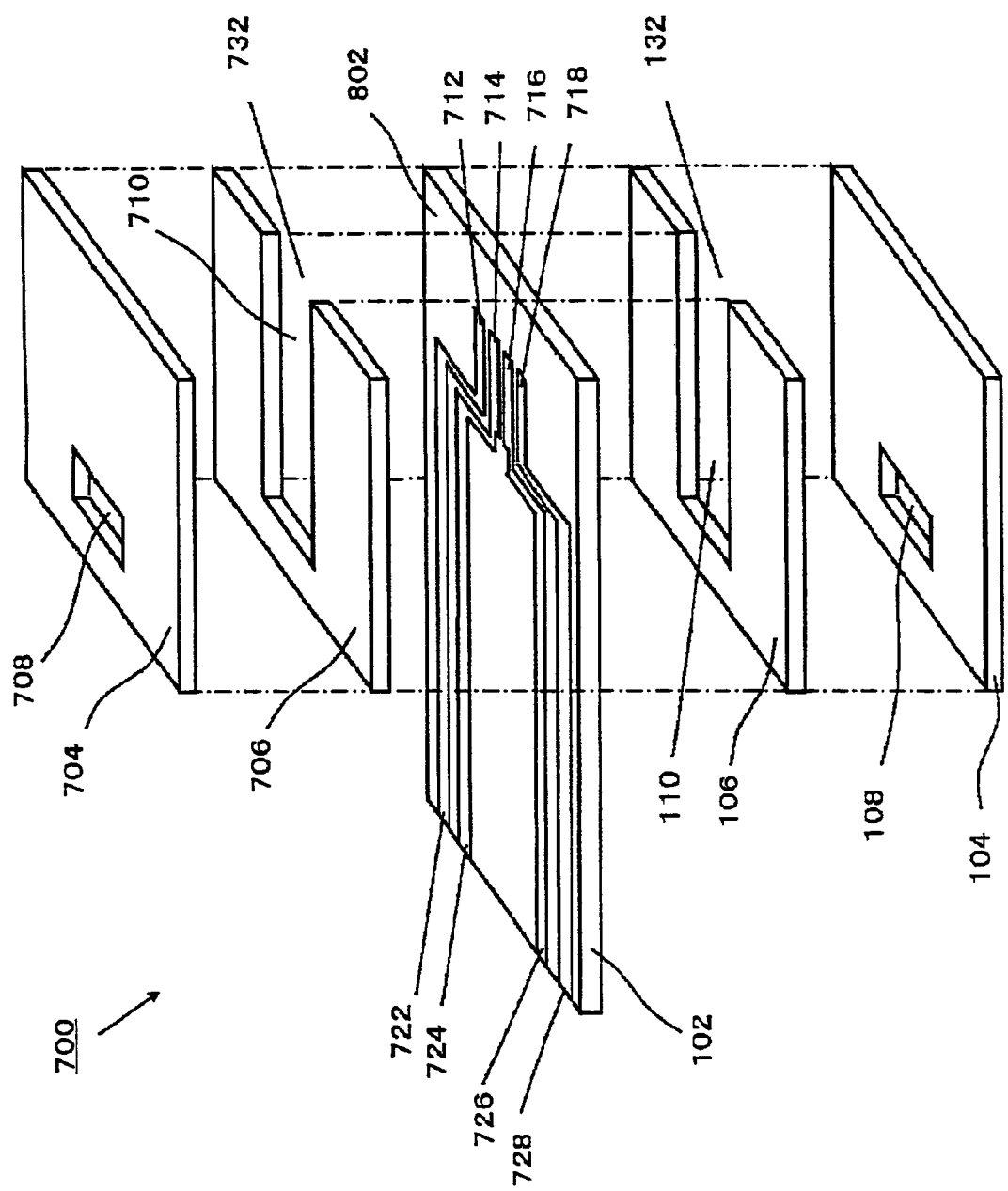
FIG. 8 is an exploded perspective view showing the structure of the device for measuring the amount of salt seen from the second face side of the first substrate in the same embodiment.

Next, a device 700 for measuring the amount of salt according to Embodiment 3 of the invention is described with reference to FIGS. 7 and 8. FIG. 7 is an exploded perspective view showing the structure of the measuring device 700 on the first face side of the first substrate, and FIG. 8 is an exploded perspective view showing the structure on the second face side of the first substrate.

The measuring device 700 is used in a method of electrochemically measuring creatinine contained in urine, i.e., sample, and measuring an electrical property of the urine in order to estimate the amount of urinary salt excretion in a day from the results of these measurements.

In the measuring device 700, a first face 702 of an insulating first substrate 102 is in contact with an insulating first spacer 106 with a slit 110, and the first substrate 102 is combined with a second substrate 104 with an air vent 108 so as to sandwich the first spacer 106. Further, a second face 802 of the first substrate 102 is in contact with an insulating second spacer 706 with a slit 710, and the first substrate 102 is combined with a third substrate 704 with an air vent 708 so as to sandwich the second spacer 706. The first substrate 102, the first spacer 106, the second substrate 104, the second spacer 706, and the third substrate 704 are made of, for example, polyethylene terephthalate.

The first substrate 102 has, on the first face 702, a first electrode 112, a second electrode 114, a first lead 122 electrically connected to the first electrode 112, and a second lead 124 electrically connected to the second electrode 114, as in the measuring device 100 of Embodiment 1. Disposed on the first electrode 112 and the second electrode 114 is a reagent layer 130 containing a creatinine quantitative reagent.

Disposed on the second face 802 of the first substrate 102 are a third electrode 712, a fourth electrode 714, and a fifth electrode 716, and a sixth electrode 718. Further disposed on the second face 802 are a third lead 722 electrically connected to the third electrode 712, a fourth lead 724 electrically connected to the fourth electrode 714, a fifth lead 726 electrically connected to the fifth electrode 716, and a sixth lead 728 electrically connected to the sixth electrode 718. The dimensions of the first substrate 102 may be suitably set; for example, the width is approximately 7 mm, the length is approximately 30 mm, and the thickness is approximately 0.7 mm.

Next, the method for producing the measuring device 700 is described.

First, palladium is sputtered onto the first face 702 of the first substrate 102 with a resin mask of an electrode pattern thereon, to form the first electrode 112, the second electrode 114, the first lead 122, and the second lead 124. The first electrode 112 and the second electrode 114 are electrically connected to the terminals of an apparatus for measuring the amount of salt, which will be described below, by the first lead 122 and the second lead 124, respectively.

Next, palladium is sputtered onto the second face 802 of the first substrate 102 with a mask of a different electrode pattern from that of the above-mentioned mask, to form the third electrode 712, the fourth electrode 714, the fifth electrode 716, the sixth electrode 718, the third lead 722, the fourth lead 724, the fifth lead 726, and the sixth lead 728. The third electrode 712, the fourth electrode 714, the fifth electrode 716, and the sixth electrode 718 are electrically connected to the terminals of the apparatus for measuring the amount of salt, described below, by the third lead 722, the fourth lead 724, the fifth lead 726, and the sixth lead 728, respectively.

Next, a given amount of an aqueous solution containing a creatinine quantitative reagent, which is the same as that of Embodiment 1, is dropped on the first electrode 112 and the second electrode 114 formed on the first face 702 of the first substrate 102 by using a microsyringe or the like. Thereafter, the first substrate 102 is left for drying in an environment at room temperature to approximately 30° C., to form the reagent layer 130. The concentration and amount of the reagent-containing aqueous solution to be applied thereto is selected depending on the characteristics and size of the necessary device; for example, they may be selected in the same manner as in Embodiment 1.

Subsequently, the second substrate 104, the first spacer 106, the first substrate 102, the second spacer 706, and the third substrate 704 are combined so that the first face 702 of the first substrate 102 contacts the first spacer 106 and the second face 802 of the first substrate 102 contacts the second spacer 706. Adhesive is applied to the portions of the respective components to be bonded, and they are laminated, pressed, and allowed to stand for bonding. Instead of this method, it is also possible to combine them without applying adhesive and then thermally or ultrasonically bond the bonding portions by using a commercially available welding machine.

When the first substrate 102, the first spacer 106, and the second substrate 104 are combined, a space is formed by the slit 110 of the first spacer 106 between the first substrate 102 and the second substrate 104, and this space serves as a first sample holding space for measuring creatinine concentration. Also, the opening of the slit 110 serves as a first sample inlet 132.

When the first substrate 102, the second spacer 706, and the third substrate 704 are combined, a space is formed by the slit 710 of the second spacer 706 between the first substrate 102 and the third substrate 704, and this space serves as a second sample holding space for measuring an electrical property of urine. Also, the opening of the slit 710 serves as a second sample inlet 732

Figure 9:
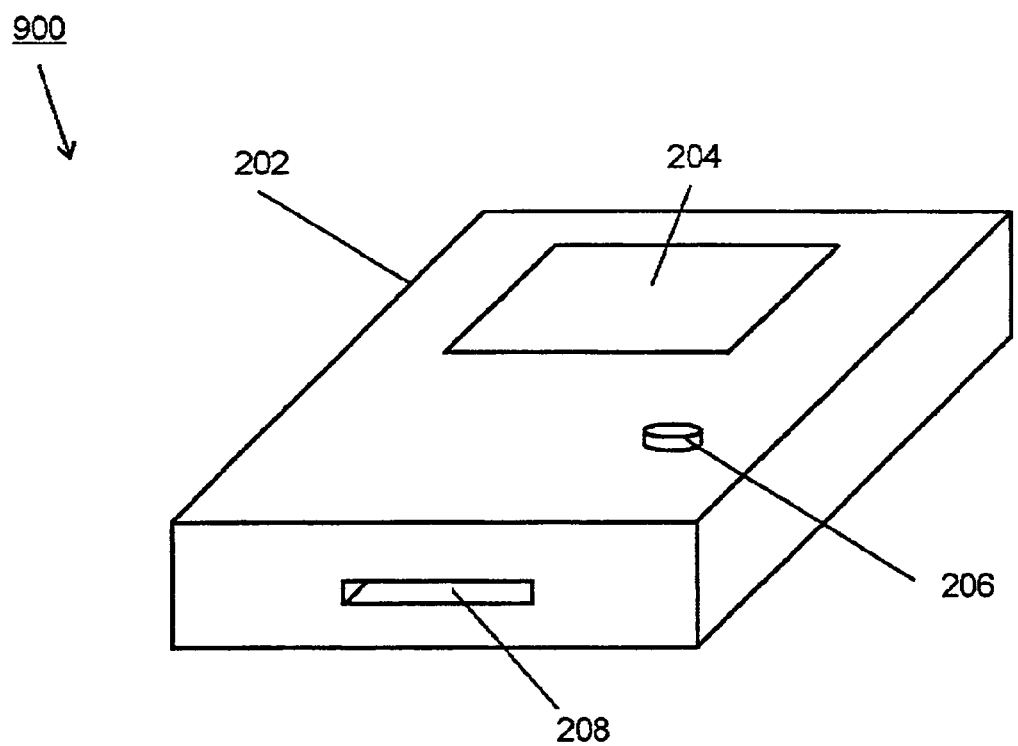
FIG. 9 is a perspective view showing the appearance of an apparatus for measuring the amount of salt in the same embodiment.
Figure 10:
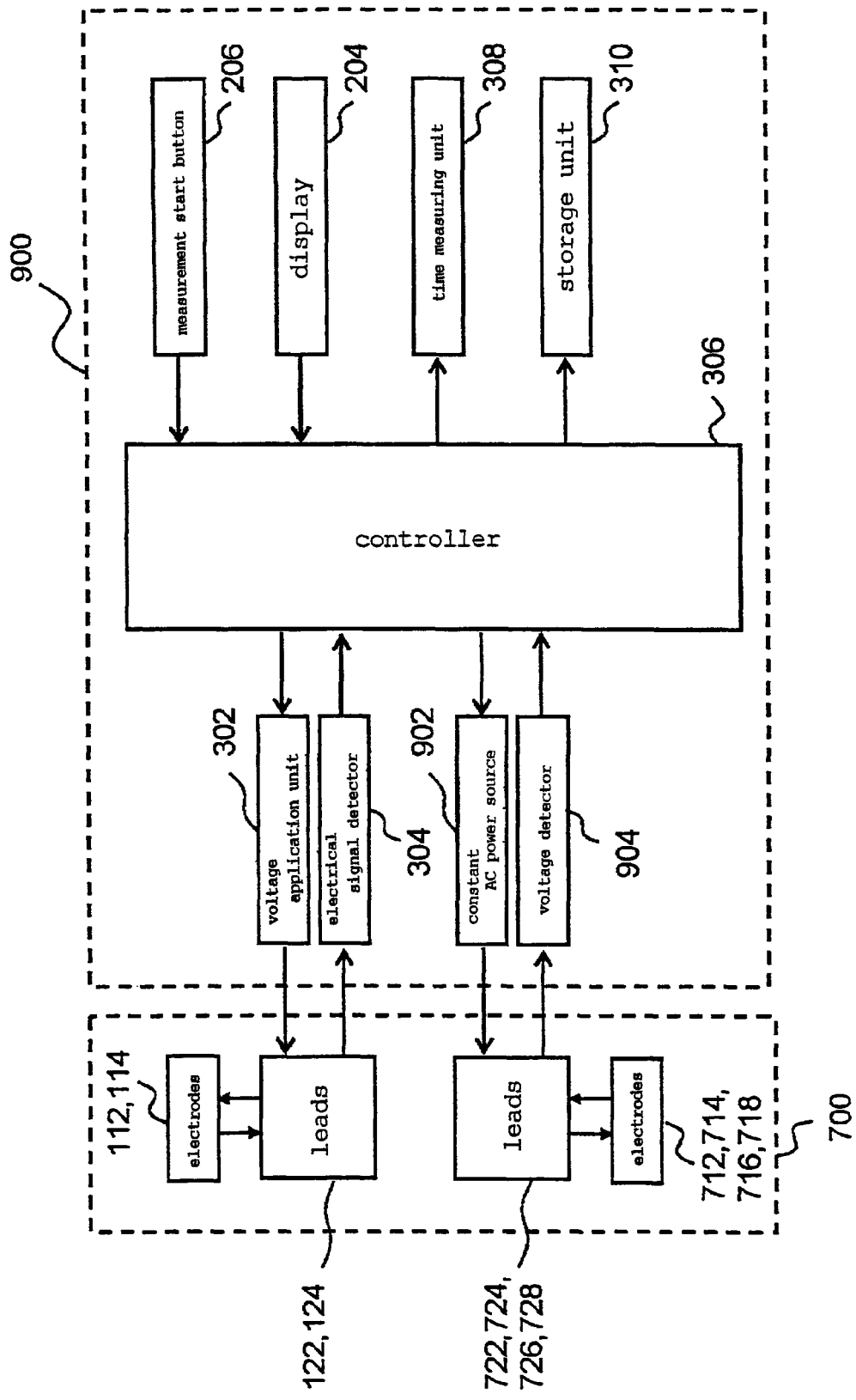
FIG. 10 is a block diagram showing the configuration of the apparatus for measuring the amount of salt in the same embodiment.

Next, an apparatus 900 for measuring the amount of salt according to this embodiment and the method for measuring the amount of salt using this apparatus are described with reference to FIGS. 9 and 10. FIG. 9 is a perspective view showing the appearance of the measuring apparatus 900, and FIG. 10 is a block diagram showing the configuration of the measuring apparatus 900.

First, the structure of the measuring apparatus 900 is described with reference to FIG. 9.

A housing 202 of the measuring apparatus 900 has a measuring device mounting port 208 for mounting the measuring device 700, a display 204 for displaying measurement results etc., and a measurement start button 206 for starting the measurement of creatinine concentration and an electrical property of urine by the measuring apparatus 900. Inside the measuring device mounting port 208 are a first terminal, a second terminal, a third terminal, a fourth terminal, a fifth terminal, and a sixth terminal, which are to be electrically connected to the first lead 122, the second lead 124, the third lead 722, the fourth lead 724, the fifth lead 726, and the sixth lead 728 of the measuring device 700, respectively.

Next, the configuration inside the housing 202 of the measuring apparatus 900 is described with reference to FIG. 10.

The housing 202 of the measuring apparatus 900 contains a voltage application unit 302, an electrical signal detector 304, a constant AC power source 902, a voltage detector 904, a controller 306, a time measuring unit 308, and a storage unit 310.

The voltage application unit 302 has the function of applying a voltage or potential to the first electrode 112 and the second electrode 114 of the measuring device 700 mounted in the measuring device mounting port 208. The voltage or potential is applied through the first terminal and the second terminal electrically connected to the first lead 122 and the second lead 124 of the measuring device 700, respectively.

The electrical signal detector 304 has the function of detecting the electrical signal from the first electrode 112 and the second electrode 114 through the first terminal and the second terminal. The electrical signal detector 304 corresponds to the detector of the invention.

The constant AC power source 902 has the function of applying a constant alternating current between the third electrode 712 and the sixth electrode 718 of the measuring device 700 mounted in the measuring device mounting port 208. The constant alternating current is applied through the third terminal and the sixth terminal electrically connected to the third lead 722 and the sixth lead 728 of the measuring device 700, respectively. The alternating current applied has, for example, a frequency of approximately 1 kHz and a current value of approximately 0.1 mA.

The voltage detector 904 has the function of detecting the voltage (effective value of alternating voltage) between the fourth electrode 714 and the fifth electrode 716 through the fourth terminal and the fifth terminal.

The storage unit 310 stores:

(I) first correlation data corresponding to a first calibration curve which indicates a correlation between creatinine concentrations and electrical signals detected by the electrical signal detector 304;

(ii) second correlation data corresponding to a second calibration curve which indicates a correlation between salt concentrations and voltages detected by the voltage detector 904; and (iii) third correlation data corresponding to a third calibration curve which indicates a correlation between the amounts of urinary salt excretion per day and salt concentrations corrected by creatinine concentration.

Examples of the storage unit 310 include memory such as RAM and ROM.

The controller 306 has the functions of:

(I) converting the electrical signal detected by the electrical signal detector 304 to creatinine concentration by referring to the first correlation data;

(II) converting the voltage detected by the voltage detector 904 to salt concentration by referring to the second correlation data;

(III) correcting the salt concentration by using the creatinine concentration thus obtained; and (IV) converting the corrected salt concentration to the amount of urinary salt excretion per day by referring to the third correlation data.

The controller 306 corresponds to the arithmetic unit of the invention. Examples of the controller 306 include microcomputers such as a CPU (Central Processing Unit).

Next, the method for measuring the amount of urinary salt using the measuring device 700 and the measuring apparatus 900 according to this embodiment is described.

First, a user inserts the lead side of the measuring device 700 into the measuring device mounting port 208 of the measuring apparatus 900. As a result, the first lead 122, the second lead 124, the third lead 722, the fourth lead 724, the fifth lead 726, and the sixth lead 728 of the measuring device 700 are electrically connected to the first terminal, the second terminal, the third terminal, the fourth terminal, the fifth terminal, and the sixth terminal inside the measuring device mounting port 208, respectively.

When the measuring device 700 is inserted into the measuring device mounting port 208, an insertion detecting switch is turned on, so that a signal is sent to the controller 306. The insertion detecting switch comprises a microswitch installed in the measuring device mounting port 208. When the controller 306 detects the insertion of the measuring device 700 from the signal sent from the insertion detecting switch, the controller 306 controls the voltage application unit 302, so that a voltage (e.g., 0.2 V) is applied between the first electrode 112 and the second electrode 114 through the first terminal and the second terminal.

Subsequently, the user brings a sample into contact with the first sample inlet 132 and the second sample inlet 732 of the measuring device 700. Due to this contact, the sample is sucked into the two sample holding spaces of the measuring device 700 from the first sample inlet 132 and the second sample inlet 732 by capillarity, so that the two sample holding spaces are filled with the sample.

When the sample comes into contact with the first electrode 112 and the second electrode 114 in the first sample holding space, a current flows between the first electrode 112 and the second electrode 114 through the sample. The resulting change in electrical signal is detected by the electrical signal detector 304.

From the signal sent from the electrical signal detector 304, the controller 306 detects the introduction of the sample into the first and second sample holding spaces.

When the controller 306 detects the introduction of the sample into the first and second sample holding spaces, the controller 306 controls the voltage application unit 302, so that the voltage applied by the voltage application unit 302 is changed to a different voltage (e.g., 0 V or open circuit). Also, upon the detection of introduction of the sample, the controller 306 causes the time measuring unit 308, which is a timer, to start measuring time.

Upon the detection of introduction of the sample into the second sample holding space, the controller 306 controls the constant AC power source 902, so that a constant alternating current (e.g., frequency 1 kHz, current value 0.1 mA) is applied between the third electrode 712 and the sixth electrode 718 through the third terminal and the sixth terminal. After a predetermined time (e.g., after five seconds) from the application of the alternating current, the voltage detector 904 measures the voltage (effective value of alternating current) between the fourth electrode 714 and the fifth electrode 716.

The controller 306 reads the second correlation data which is stored in the storage unit 310 and which indicates a correlation between salt concentrations and voltages detected by the voltage detector 904, and refers to it. As a result, the voltage detected by the voltage detector 904 is converted to the salt concentration in the sample. The salt concentration thus determined is displayed on the display 204.

When the sample comes into contact with the reagent layer 130 in the first sample holding space, potassium ferricyanide contained in the reagent layer 130 dissolves in the sample. The dissolution of potassium ferricyanide in the sample produces trivalent hexacyanoferrate. The produced trivalent hexacyanoferrate directly reacts with creatinine contained in the sample to form an oxidation product of creatinine and tetravalent hexacyanoferrate.

When the controller 306 determines from the signal sent from the time measuring unit 308 that a predetermined time (e.g., 60 seconds) has passed, the controller 306 controls the voltage application unit 302, so that a different voltage is applied again between the first electrode 112 and the second electrode 114 (for example, such a voltage that the first electrode 112 is +0.5 to +0.6 V relative to the second electrode 114). After a certain time (e.g., five seconds) from the voltage application, an electrical signal such as the current flowing between the first electrode 112 and the second electrode 114 is measured by the electrical signal detector 304. At this time, the tetravalent hexacyanoferrate is oxidized at the first electrode 112. The electrical signal measured by the electrical signal detector 304 is dependent on the creatinine concentration in the sample.

The controller 306 reads the first correlation data which is stored in the storage unit 310 and which indicates a correlation between electrical signals and creatinine concentrations, and refers to it. As a result, the electrical signal detected by the electrical signal detector 304 is converted to the creatinine concentration in the sample.

Thereafter, the controller 306 corrects the salt concentration by using the creatinine concentration thus obtained. The controller 306 then reads the third correlation data which is stored in the storage unit 310 and which corresponds to the third calibration curve indicating a correlation between the amounts of urinary salt excretion per day and salt concentrations corrected by creatinine concentration, and refers to it. As a result, the corrected salt concentration is converted to the amount of urinary salt excretion per day.

The creatinine concentration and the amount of urinary salt excretion per day, determined in the above manner, are displayed on the display 204. Upon the display of the creatinine concentration and the amount of urinary salt excretion per day on the display 204, the user can recognize that the measurement has been completed. It is preferred to store the creatinine concentration and the amount of urinary salt excretion per day in the storage unit 310 together with the time measured by the time measuring unit 308.

According to the measuring apparatus 900, based on the salt concentration corrected by using the creatinine concentration measured with high accuracy, the amount of urinary salt excretion per day is calculated. It is therefore possible to obtain the amount of urinary salt excretion per day with high accuracy.

This embodiment has shown an example in which hexacyanoferrate is used as the creatinine quantitative reagent, but hexacyanoruthenate may also be used instead. In the case of using hexacyanoruthenate, it is also possible to quantify creatinine contained in a sample with better accuracy than conventional measuring devices without being affected by interferents including ions species such as salt, urea, amino acids, and sugars.

In this embodiment, the measuring device may include two or more reagent layers in the same manner as in Embodiment 1.

In this embodiment, the voltage applied by the voltage application unit does not always need to be changed to a different voltage as long as a current dependent on the creatinine concentration is obtained.

In this embodiment, the voltage between the first electrode and the second electrode may be any voltage at which the tetravalent hexacyanoferrate is oxidized.

In this embodiment, in the same manner as in Embodiment 1, the time (reaction time) from the detection of introduction of a sample to the detection of an electrical signal is not to be construed as limiting.

This embodiment has shown an example in which an electrical signal is detected five seconds after the application of a voltage between the first electrode and the second electrode, but this time is not to be construed as limiting.

This embodiment has shown an example in which the storage unit stores the first to third correlation data, but this is not to be construed as limiting. Instead, the storage unit may store correlation data indicating a correlation between electrical signals detected by the electrical signal detector, voltages detected by the voltage detector, and amounts of urinary salt excretion per unit time (e.g., per day). In this case, there is no need to determine creatinine concentration or salt concentration. The amount of urinary salt excretion per unit time is directly determined from the electrical signal detected by the electrical signal detector and the voltage detected by the voltage detector.

In order to facilitate the introduction of a sample into the sample holding spaces of the device for measuring the amount of salt, a lecithin layer similar to that of Embodiment 1 may be formed on the inner walls of the second substrate and the third substrate.

The apparatus for measuring the amount of salt may further include a recorder for recording measurement results in a storage medium such as an SD card.

The apparatus for measuring the amount of salt may further include a transmitter for transmitting measurement results to outside of the measuring apparatus.

The apparatus for measuring the amount of salt may further include a receiver for receiving the results of analysis by an analytical department, an analytical laboratory, or the like.

EXAMPLES

Example 1

The following experiment was conducted to confirm the effect of the method for measuring the concentration of creatinine according to the invention. In this example, hexacyanoferrate was used as a metal complex contained in a creatinine quantitative reagent, and potassium ferricyanide was used as a complex salt thereof.

First, an aqueous solution of 400 mM dipotassium hydrogen phosphate (available from Wako Pure Chemical Industries, Ltd.; this was also used in the following examples and reference examples) and an aqueous solution of 400 mM potassium dihydrogen phosphate (available from Wako Pure Chemical Industries, Ltd.; this was also used in the following examples and reference examples) were prepared. While monitoring with a pH meter, the two aqueous solutions were mixed to adjust the pH of the resultant mixed aqueous solution to 6. In this way, a 400 mM phosphate buffer solution (pH=6) was prepared. In this buffer solution was dissolved potassium ferricyanide at a concentration of 400 mM.

The aqueous solution thus obtained was introduced into a glass cell container, and a first electrode, a second electrode, and a third electrode were immersed in the aqueous solution in the cell container. The first electrode was a gold electrode (electrode area 2 mm$^2$). The second electrode was prepared by winding up a 5-cm long platinum wire in a coil. The third electrode was an Ag/AgCl (saturated KCl aqueous solution) reference electrode. All the electrodes are commercial products available from BAS Inc. The connecting terminals of the first electrode, the second electrode, and the third electrode were sequentially connected to the connecting terminals of the working electrode, counter electrode, and reference electrode of an electrochemical analyzer (ALS-660A available from ALS Co., Ltd.).

Subsequently, a small amount of a creatinine aqueous solution with a concentration of 500 mM (available from Wako Pure Chemical Industries, Ltd.; this was also used in the following examples and reference examples) was added to the aqueous solution in the cell container. The amount of the creatinine aqueous solution added was adjusted in each measurement so that the concentration of creatinine contained in the aqueous solution in the cell container was a predetermined value.

Upon the addition of creatinine, time measurement was started, and 10 minutes after the addition of creatinine, a potential of 0.5 V was applied to the first electrode relative to the third electrode. Five seconds after the potential application, the current value was measured. This experiment was conducted at room temperature (approximately 25° C.)

The creatinine concentration in the aqueous solution contained in the cell container was varied to 0, 1, 2, 5, 10, 20, 30, 40, and 50 mM, and measurements were made in the manner as described above.

FIG. 11 is a graph of the measured current values plotted as a function of creatinine concentration. In FIG. 11, the abscissa represents the concentration (mM) of creatinine contained in the aqueous solution in the cell container, and the ordinate represents the measured current values (μA). As is clear from FIG. 11, the current value increases linearly with (i.e., in proportion to) the increase in creatinine concentration in the aqueous solution in the cell container, which indicates a high correlation between the current values and the creatinine concentrations. Therefore, it is understood that the method for measuring the concentration of creatinine according to the invention can provide creatinine quantification based on current values obtained.

After the measurements, the aqueous solutions of the different creatinine concentrations remaining in the cell container were subjected to a column chromatography to analyze the reaction products. The analysis result showed that these aqueous solutions in the cell container contained tetravalent hexacyanoferrate. Also, the amount of tetravalent hexacyanoferrate produced was a maximum of 4 molecules per 1 molecule of creatinine. From the above analysis result, the reactions in the method for measuring the concentration of creatinine according to the invention may be explained as follows.

In the sample, trivalent hexacyanoferrate reacts with creatinine in the presence of the phosphate buffer, so that it is reduced and converted to tetravalent hexacyanoferrate. That is, creatinine donates electrons to trivalent hexacyanoferrate, thereby being oxidized. In this reaction, it can be assumed that creatinine was oxidized by a maximum of 4 electrons. The first electrode is under such a potential that electrons are received from tetravalent hexacyanoferrate. Thus, the produced tetravalent hexacyanoferrate is electrochemically oxidized at the first electrode. As a result, a current flows through the first electrode. The concentration of tetravalent hexacyanoferrate produced in a certain time is dependent on the creatinine concentration. Also, the oxidation current of the tetravalent hexacyanoferrate is dependent on the concentration of tetravalent hexacyanoferrate in the sample. Therefore, the current value obtained is dependent on the creatinine concentration.

Example 2

Next, the following experiment was conducted to check the pH range preferable in the method for measuring the concentration of creatinine according to the invention. Since the sample preparation method and the configuration of the apparatus used in the experiment and the experiment procedure are the same as those of Example 1, the explanation thereof is omitted. However, in this example, the creatinine concentration in the sample was set to 27 mM. Also, the pH of the phosphate buffer solution added to the sample was varied to 2, 2.5, 3, 4, 5, 6, 7, 8, and 9, and measurements were made in the same manner as in Example 1.

Table 1 shows the measurement results of current values. In the pH range of 2.5 to 7, in particular, the range of 3 to 6, the current value is significantly high and the current value is stable. This result shows that in this pH range, creatinine is quantified with particularly high sensitivity and high reproducibility. Of the above-mentioned ranges, the pH 5 to 6 can be obtained by a phosphate buffer. Also, it is found that the speed of the reaction between creatinine and trivalent hexacyanoferrate increases in the presence of a phosphate buffer. It is therefore preferable to mix a phosphate buffer with a sample to adjust the pH to 5 to 6. Also, such a pH is obtained by a hydrogen phosphate ion and a dihydrogen phosphate ion. It is thus thought that the preferable phosphate buffer contains, for example, a combination of dipotassium hydrogen phosphate or disodium hydrogen phosphate and potassium dihydrogen phosphate or sodium dihydrogen phosphate. Also, in the pH range of 2.5 to 7, current values can also be obtained, so creatinine quantification is possible.

TABLE 1

| | pH | | | | | | | | |
|---|---|---|---|---|---|---|---|---|---|
| | 2 | 2.5 | 3 | 4 | 5 | 6 | 7 | 8 | 9 |
| Current (µA) | 0.1 | 1.6 | 2.7 | 2.9 | 2.9 | 2.8 | 1.6 | 0.4 | 0.2 |

Example 3

Next, the following experiment was conducted to examine the influence of coexistent substances that may be contained in samples on the method for measuring the concentration of creatinine according to the invention.

Examples of coexistent substances that may be contained in biological samples include ion species, enzyme denaturants, products of enzyme reaction of creatinine, sugars, and amino acids. Thus, as representative coexistent substances, this example used: NaCl, which produces ion species when dissolved in a sample; urea, which is an enzyme denaturant; creatine, sarcosine, and glycine, which are products of enzyme reaction of creatinine; glucose, which is a sugar; and histidine, taurine, glutamine, and serine, which are amino acids.

In the same procedure as that of Example 1, a phosphate buffer solution (pH=6) with a concentration of 50 mM was prepared, and each of the coexistent substances was dissolved in the buffer solution at a predetermined concentration. The resultant sample was measured at a room temperature of 25° C. Also, the sample was heated to 60° C. to accelerate the reaction and measured at 60° C. Except for this, the sample preparation method, the configuration of the apparatus, and the experiment procedure are the same as those of Example 1, so the explanation thereof is omitted.

Table 2 shows that the coexistent substances used, the concentrations thereof, and the current values measured. In Table 2, sample 1 is a phosphate buffer solution that contains no coexistent substance and contains 3 mM of creatinine. Also, samples 2 to 11 contain the respective coexistent substances shown in Table 2 and contain no creatinine. In Table 2, the measured current values are relative values with respect to the measured current value of sample 1 which was defined as 100.

Table 2 indicates that all the samples containing the different coexistent substances did not exhibit an effective current, compared with sample 1 containing creatinine and containing no coexistent substance. This result has demonstrated that the method for measuring the concentration of creatinine according to the invention is not affected even if any of NaCl, urea, creatine, sarcosine, glycine, glucose, histidine, taurine, glutamine, and serine is contained in a sample.

TABLE 2

| | Coexistent substance | Concentration (mM) | Current | |
|---|---|---|---|---|
| | | | 25° C. | 60° C. |
| Sample 1 | None | — | 100.0 | 100.0 |
| Sample 2 | NaCl | 500 | <0.5 | — |
| Sample 3 | Urea | 1000 | <0.5 | — |
| Sample 4 | Creatine | 3 | <0.1 | <0.1 |
| Sample 5 | Sarcosine | 3 | <0.1 | <0.1 |
| Sample 6 | Glycine | 3 | <0.1 | <0.1 |
| Sample 7 | Glucose | 10 | <0.1 | <0.1 |
| Sample 8 | Histidine | 3 | <0.1 | <0.1 |
| Sample 9 | Taurine | 3 | <0.1 | <0.1 |
| Sample 10 | Glutamine | 3 | <0.1 | <0.1 |
| Sample 11 | Serine | 3 | <0.1 | <0.1 |

On the other hand, it is known that in conventional methods in which creatinine is quantified in an alkaline solution with the use of an oxidant, such as the Jaffe method, the influence of sugars and amino acids on measurement results is large. This is because in an alkali solution, picric acid easily reacts with many organic molecules just as creatinine.

A similar experiment was conducted by a conventional enzymatic method as comparative examples. First, a 50 mM phosphate buffer solution (pH=7) was prepared which contained 7 U/mL creatinine amidohydrolase (creatininase) (CNH-311 available from TOYOBO CO., LTD.), 10 U/mL creatine amidinohydrolase (creatinase)(CRH-221 available from TOYOBO CO., LTD.), 5 U/mL sarcosine oxidase (SAO-351 available from TOYOBO CO., LTD.), and 100 mM potassium ferricyanide.

A sample 12 was prepared by adding creatinine to the phosphate buffer solution at a concentration of 3 mM.

A sample 13 was prepared by adding NaCl as a coexistent substance to the sample 12 at a concentration of 0.5 M.

A sample 14 was prepared by adding urea as a coexistent substance to the sample 12 at a concentration of 1M.

Using samples 12 to 14, an experiment was conducted in the same manner as in this Example except that these samples were heated to 40° C. to accelerate the reaction.

Table 3 shows the results of these comparative examples. The current values shown therein are relative values with respect to the current value of sample 12 which was defined as 100.

As is understood from Table 3, when 0.5 M NaCl or 1 M urea was present in the sample, the current value derived from creatinine decreased significantly, compared with when there was no coexistent substance. This result is probably due to the denaturation of the enzyme protein by the high concentration of NaCl or urea. These coexistent substances have been found to decrease the activity of the enzymes used in the measurements to 25 to 80%. The decrease in the current value is probably because the enzyme denaturation results in decreased enzyme activity, thereby reducing the reaction which proceeds in a certain period of time. It is thought that this tendency also exists at room temperature.

TABLE 3

| | Coexistent substance | Current |
|---|---|---|
| Sample 12 | None | 100.0 |
| Sample 13 | 0.5 M NaCl | 89.8 |
| Sample 14 | 1 M Urea | 96.4 |

The above results have shown that the method for measuring the concentration of creatinine according to the invention can quantify creatinine contained in a sample with better accuracy than conventional measuring methods without being affected by coexistent components such as ion species, urea, products of enzyme reaction of creatinine, sugars, and amino acids.

Example 4

The following experiment was conducted to confirm the effect of the method for measuring the concentration of creatinine according to the invention.

In this example, a potassium salt of tetravalent anion hexacyanoruthenate (available from Mitsuwa Chemicals Co., Ltd.) represented by the following formula (8) was used as the creatinine quantitative reagent.

$$K_4[Ru(CN)_6] \qquad (8)$$

First, an aqueous solution of 200 mM dipotassium hydrogen phosphate and an aqueous solution of 200 mM potassium dihydrogen phosphate were prepared. While monitoring with a pH meter, the two aqueous solutions were mixed to adjust the pH of the resultant mixed aqueous solution to 6. In this way, a 200 mM phosphate buffer solution (pH=6) was prepared. In this buffer solution was dissolved the potassium salt of hexacyanoruthenate represented by formula (8) at a concentration of 1 mM.

Since the configuration of the cell and measuring apparatus used in this example is the same as that of Example 1, the explanation thereof is omitted.

Next, a small amount of a creatinine aqueous solution with a concentration of 500 mM was added to the aqueous solution in the cell container. The amount of the creatinine aqueous solution added was adjusted in each measurement so that the concentration of creatinine contained in the aqueous solution in the cell container was a predetermined value. The creatinine concentration in the aqueous solution contained in the cell container was varied to 0, 8, 16, 32, and 64 mM, and measurements were made in the following manner.

After the addition of the creatinine aqueous solution, using an electrochemical analyzer (ALS-660A available from ALS Co., Ltd.), the potential applied to the first electrode was swept from 0.5 V to 1 V relative to the third electrode and then swept from 1 V to 0.5 V. The current which flowed at this time was measured. The potential sweep rate was set to 1 mV/second.

FIG. 12 shows the measurement results (cyclic voltammogram). In FIG. 12, curves A to E represent the measurement results for the creatinine concentrations of 0, 8, 16, 32, and 64 mM, respectively. When creatinine was not present, the redox reaction of hexacyanoruthenate on the first electrode, with the redox potential being near 0.75 V, was observed. When creatinine was added, the current at potentials higher than 0.8 V increased significantly. The above results indicate that creatinine is oxidized by the oxidized form of hexacyanoruthenate, and that the resultant reduced form of hexacyanoruthenate is oxidized on the first electrode. That is, they show that the electrochemical, catalytic oxidation reaction of creatinine proceeds via hexacyanoruthenate.

The oxidation current values at 0.9 V for the respective samples with the different creatinine concentrations were obtained from the cyclic voltammogram shown in FIG. 12, and the differences from the oxidation current value for the creatinine concentration of 0 were calculated. FIG. 13 is a graph of the oxidation current value differentials plotted as a function of creatinine concentration. As shown in FIG. 13, the oxidation current value obtained increased with the increase in creatinine concentration. Therefore, it has been found that obtaining the oxidation current value by cyclic voltammetry as in this example permits creatinine quantification.

In this example, the oxidation current was measured by cyclic voltammetry, but this is not to be construed as limiting. Instead, it is also possible, for example, to apply a constant potential of 0.9 V to the first electrode relative to the third electrode and measure the oxidation current flowing after a certain time (e.g., 3 minutes) from the addition of creatinine. In this case, also, the oxidation current value increases depending on the creatinine concentration in the sample, so creatinine quantification is possible.

Example 5

The following experiment was conducted to confirm the effect of the method for measuring the concentration of creatinine according to the invention.

In this example, potassium ferricyanide was used as a metal complex of hexacyanoferrate, and cationic guar gum was used as a cationic hydrophilic polymer. Also, in the same procedure as that of Embodiment 1, a device for measuring the concentration of creatinine having a structure shown in FIG. 1 was produced. In this example, commercially available guar hydroxypropyltrimonium chloride was used as cationic guar gum.

The reagent-containing aqueous solution used to form the reagent layer 130 was prepared as follows. First, an aqueous solution of 400 mM dipotassium hydrogen phosphate and an aqueous solution of 400 mM potassium dihydrogen phosphate were prepared. Subsequently, while monitoring with a pH meter, the two aqueous solutions were mixed to adjust the pH of the resultant mixed aqueous solution to 6. In this way, a 400 mM phosphate buffer solution (pH=6) was prepared. Lastly, potassium ferricyanide was dissolved in this buffer solution at a concentration of 100 mM, and cationic guar gum was dissolved at a concentration of 0.25% by weight. In this way, the reagent-containing aqueous solution was obtained.

The aqueous solution prepared in the above manner was dropped in an amount of 1.4 µL on the first electrode 112 and the second electrode 114, to form the reagent layer 130. The area of the region on which the reagent layer 130 was formed was set to 3 mm². Also, the volume of the sample holding space of the produced device for measuring the concentration of creatinine was 0.6 µL.

Also, as a reference example, a device for measuring the concentration of creatinine having a structure shown in FIG. 1 was produced in the same manner as in Example 1, except that cationic guar gum was not added to the aqueous solution used to form the reagent layer.

A terminal of an electrochemical analyzer (ALS-660A available from ALS Co., Ltd.) for the working electrode and two terminals for the counter and reference electrodes were connected to the first lead and the second lead of the device for measuring the concentration of creatinine, respectively. Thereafter, an aqueous solution of creatinine, serving as a sample, was brought into contact with the sample inlet of the device for measuring the concentration of creatinine, so that 0.6 µL of the sample was introduced into the sample holding space. After 60 seconds from the introduction of the sample, using the electrochemical analyzer, a voltage was applied so that the first electrode was +0.6 V relative to the second electrode. After 10 seconds from the voltage application, the current flowing between the first electrode and the second electrode was measured. The above experiment was conducted at room temperature (approximately 25° C.)

Samples with creatinine concentrations of 0, 10, 30, and 40 mM were measured in the above manner.

FIG. 14 a is graph of the current values measured with the device for measuring the concentration of creatinine of Example 5, plotted as a function of creatinine concentration. In FIG. 14, the abscissa represents the concentration (mM) of creatinine contained in the samples, and the ordinate represents the measured current values (µA). As is clear from FIG. 14, the current value obtained increases linearly with (i.e., in proportion to) the increase in creatinine concentration in the samples, which indicates a high correlation between the current values and the creatinine concentrations.

FIG. 15 is a graph showing variation (coefficient of variation) of the current values measured with the devices for measuring the concentration of creatinine of Example 5 and the reference example. In FIG. 15, the abscissa represents the concentration (mM) of creatinine contained in the samples, while the ordinate represents the coefficient of variation (%). Also, the white bars represent data on Example 5, while the black bars represent data on the reference example.

As is understood from FIG. 15, in the measurements of all the samples with the different creatinine concentrations, the device for measuring the concentration of creatinine of Example 5 exhibits low coefficients of variation, compared with the reference example. This result indicates that the addition of cationic guar gum to the reagent layer enhances the reproducibility of measurements of creatinine concentration.

INDUSTRIAL APPLICABILITY

The invention is useful in the quantification of creatinine contained in a sample, in particular, a biological sample such as urine.

| Reference Signs List | |
|---|---|
| 100, 400 | Device for Measuring Creatinine Concentration |
| 102 | First Substrate |
| 104 | Second Substrate |
| 106 | Spacer (First Spacer) |
| 108, 708 | Air Vent |
| 110, 710 | Slit |
| 112 | First Electrode |
| 114 | Second Electrode |
| 122 | First Lead |
| 124 | Second Lead |
| 130 | Reagent Layer |
| 132 | Sample Inlet (First Sample Inlet) |
| 200, 500 | Apparatus for Measuring Creatinine Concentration |
| 202 | Housing |
| 204 | Display |
| 206 | Measurement Start Button |
| 208 | Measuring Device Mounting Port |
| 302 | Voltage Application Unit |
| 304 | Electrical Signal Detector |
| 306 | Controller |
| 308 | Time Measuring Unit |
| 310 | Storage Unit |
| 502 | Light Source |
| 504 | Light Receiver |
| 700 | Device for Measuring the Amount of Salt |
| 702 | First Face |
| 704 | Third Substrate |
| 706 | Second Spacer |
| 712 | Third Electrode |
| 714 | Fourth Electrode |
| 716 | Fifth Electrode |
| 718 | Sixth Electrode |
| 722 | Third Lead |
| 724 | Fourth Lead |
| 726 | Fifth Lead |
| 728 | Sixth Lead |
| 732 | Second Sample Inlet |
| 802 | Second Face |
| 900 | Apparatus for Measuring the Amount of Salt |
| 902 | Constant AC Power Source |
| 904 | Voltage Detector |

The invention claimed is:

1. A method for measuring a concentration of creatinine contained in urine or blood, comprising the steps of:
   (A) mixing urine or blood containing creatinine with a creatinine quantitative reagent containing a metal complex of at least one of hexacyanoferrate and hexacyanoruthenate in the absence of picric acid and in the absence of any enzyme responsive to creatinine, to cause the creatinine to reduce the metal complex,
   wherein, the urine or blood after the mixing in step (A) has a pH of not less than 2.5 and not more than 7;
   (B) electrochemically measuring an amount of the metal complex reduced in step (A); and
   (C) determining a concentration of the creatinine contained in the urine or blood from the amount of the reduced metal complex measured in step (B).

2. The method for measuring a concentration of creatinine in accordance with claim 1, wherein after the mixing in step (A), the urine or blood has a pH of 3 or more and 6 or less.

3. The method for measuring a concentration of creatinine in accordance with claim 1, wherein in step (A), the urine or blood is further mixed with a phosphate buffer.

4. The method for measuring a concentration of creatinine in accordance with claim 1, wherein in step (A), the urine or blood is further mixed with a phosphate buffer so that a pH of the sample is adjusted to 5 to 6.

5. The method for measuring a concentration of creatinine in accordance with claim 1, wherein in step (A), the urine or blood is further mixed with a cationic hydrophilic polymer.

6. The method for measuring a concentration of creatinine in accordance with claim 5, wherein the cationic hydrophilic polymer is cationic guar gum.

7. The method for measuring a concentration of creatinine in accordance with claim 1,
wherein step (B) comprises the steps of:
(D) bringing the urine or blood into contact with two or more electrodes and applying a voltage between the two electrodes; and
(E) detecting a current value or an amount of electric charge flowing between the two electrodes, and
in step (C), the concentration of the creatinine contained in the urine or blood is determined from the current value or the amount of electric charge detected in the step (E).

\* \* \* \* \*